United States Patent
Leblanc et al.

(10) Patent No.: US 6,583,126 B2
(45) Date of Patent: Jun. 24, 2003

(54) PHOSPHONIC ACID DERIVATIVES AS INHIBITORS OF PROTEIN TYROSINE PHOSPHATASE 1B (PTP-1B)

(75) Inventors: Yves Leblanc, Kirkland (CA); Claude Dufresne, Dollard des Ormeaux (CA); Scheigetz John, Dollard des Ormeaux (CA); Cheuk Kun Lau, Ile Bizard (CA); Chun Sing Li, Dollard des Ormeaux (CA); Patrick Roy, Dollard des Ormeaux (CA); Michael Boyd, Pointe-Claire (CA); Zhaoyin Wang, Kirkland (CA)

(73) Assignee: Merck Erosst Canada & Co., Kirkland ( * ) Notice: Subject to any disclaimer, the term of this patent is extended or adjusted under 35 U.S.C. 154(b) by 112 days.

(21) Appl. No.: 09/745,222

(22) Filed: Dec. 21, 2000

(65) Prior Publication Data

US 2002/0052344 A1 May 2, 2002

Related U.S. Application Data

(60) Provisional application No. 60/171,426, filed on Dec. 22, 1999.

(51) Int. Cl.$^7$ .......................... C07F 9/38; A61K 31/662
(52) U.S. Cl. ........................ 514/75; 514/102; 514/114; 514/112; 562/8; 562/11
(58) Field of Search .................................. 562/8, 11, 12, 562/15; 514/75, 102, 114, 115, 120, 112, 126

(56) References Cited

U.S. PATENT DOCUMENTS 6,066,715 A    5/2000 Desmarais et al.

FOREIGN PATENT DOCUMENTS

| WO | WO97/40017  | 10/1997 |
| WO | WO 98/20156 | 5/1998  |
| WO | WO 99/31066 | 6/1999  |
| WO | WO 99/47529 | 9/1999  |
| WO | WO 00 17211 | 3/2000  |

OTHER PUBLICATIONS

Ahmad, et al., J. Biol. Chem., vol. 270, pp. 20503–20508, 1995.
Bin, et al., Tetrahedron, vol. 52, No. 30, pp. 9963–9970.
Caplan, et al., Bioorganic & Medicinal Chem. Letters, vol. 8, No. 5, pp. 515–520.
Charbonneau, et al, Proc. Natl. Acad Sci. USA, vol. 86, pp. 5252–5256, 1989.
Fishcer, et al., Science, vol. 253, pp. 401–406, 1991.
Goldstein, Receptor vol. 3, pp. 1–15, 1993.
Kotoris, et al., J. Org. Chem., vol. 63, pp. 8052–8057, 1998.
Seely, et al., Diabetes, vol. 45, pp. 1379–1385, 1996.
Taylor, et al., Bioorg. Med. Chem., vol. 6(9), pp. 1457–1468, 1998.
Taylor, et al., Bioorg. Med. Chem., vol. 6, p. 2235, 1998.
Taylor, et al., Tetrahedron Letters, vol. 8, No. 45, pp. 8089–8092, 1996.
Taylor, et al., Tetrahedron, No. 54, pp. 1691–1714, 1998.
Wang, et al., Bioorg. Med. Chem., Let., vol. 8(4), pp. 345–350, 1998.
White, et al., J. Biol. Chem., vol. 269, pp. 1–4, 1994.
Yokomatsu, et al., Tetrahedron, vol. 54, No. 32, pp. 9341–9356.
Burke, et al., Bioorg. Med. Chem. Letters, vol. 9, pp. 347–352, 1999.
Yao, et al., Tetrahedron, vol. 55, pp. 2865–2874, 1999.
Beaulieu, et al.., J. Med. Chem., vol. 42, pp. 1757–1766, 1999.
Kotoris, et al., Bioorg. Med. Chem., vol. 8, pp. 3275–3280, 1998.
Charifson, et al., Biochemistry, US, American Chemical Society, 1997, pp. 6283–6293, vol. 36–No. 21.
Desmarais, S., et al., Biochemical Journal, 1999, pp. 219–223, vol. 337–No. 2.
Taing, M., Biochemistry, 1999, pp. 3793–3803, vol. 38 –No. 12.

*Primary Examiner*—Jean F. Vollano
(74) *Attorney, Agent, or Firm*—James L. McGinnis; Melvin Winokur

(57) ABSTRACT

The invention encompasses the novel class of compounds represented by formula I which are inhibitors of the PTP-1B enzyme.

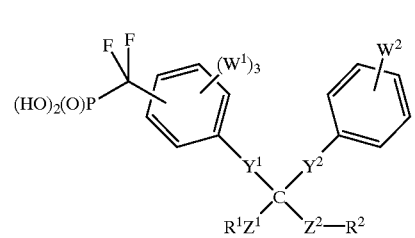

The invention also encompasses pharmaceutical compositions and methods of treating or preventing PTP-1B mediated diseases, including diabetes, obesity, and diabetes-related diseases.

17 Claims, No Drawings

PHOSPHONIC ACID DERIVATIVES AS INHIBITORS OF PROTEIN TYROSINE PHOSPHATASE 1B (PTP-1B)

CROSS REFERENCE TO RELATED APPLICATION

This application is based on and claims priority from U.S. Provisional Application No. 60/171,426, which was filed on Dec. 22, 1999, and which is incorporated by reference into this application. Commonly assigned U.S. application Ser. No. 09/398,356, filed on Sep. 17, 1999, now U.S. Pat. No. 6,174,874, and commonly assigned U.S. application Ser. Nos. 09/745,220, 09/745,199 and 09/745,211, all filed on even date herewith, contain related subject matter.

BACKGROUND OF THE INVENTION

This invention relates to a novel class of phosphonic acid derivatives that are inhibitors of PTP-1B.

Protein tyrosine phosphatases are a large family of transmembrane or intracellular enzymes that dephosphorylate substrates involved in a variety of regulatory processes (Fischer et al., 1991, Science 253:401–406). Protein tyrosine phosphatase-1B (PTP-1B) is a ~50 kd intracellular protein present in abundant amounts in various human tissues (Charbonneau et al., 1989, Proc. Natl. Acad. Sci. USA 86:5252–5256; Goldstein, 1993, Receptor 3:1–15).

Determining which proteins are substrates of PTP-1B has been of considerable interest. One substrate which has aroused especial interest is the insulin receptor. The binding of insulin to its receptor results in autophosphorylation of the receptor, most notably on tyrosines 1146, 1150, and 1151 in the kinase catalytic domain (White & Kahn, 1994, J. Biol. Chem. 269:1–4). This causes activation of the insulin receptor tyrosine kinase, which phosphorylates the various insulin receptor substrate (IRS) proteins that propagate the insulin signaling event further downstream to mediate insulin's various biological effects.

Seely et al., 1996, Diabetes 45:1379–1385 ("Seely") studied the relationship of PTP-1B and the insulin receptor in vitro. Seely constructed a glutathione S-transferase (GST) fusion protein of PTP-1B that had a point mutation in the PTP-1B catalytic domain. Although catalytically inactive, this fusion protein was able to bind to the insulin receptor, as demonstrated by its ability to precipitate the insulin receptor from purified receptor preparations and from whole cell lysates derived from cells expressing the insulin receptor.

Ahmad et al., 1995, J. Biol. Chem. 270:20503–20508 used osmotic loading to introduce PTP-1B neutralizing antibodies into rat KRC-7 hepatoma cells. The presence of the antibody in the cells resulted in an increase of 42% and 38%, respectively, in insulin stimulated DNA synthesis and phosphatidyinositol 3' kinase activity. Insulin receptor autophosphorylation and insulin receptor substrate-1 tyrosine phosphorylation were increased 2.2 and 2.0-fold, respectively, in the antibody-loaded cells. The antibody-loaded cells also showed a 57% increase in insulin stimulated insulin receptor kinase activity toward exogenous peptide substrates.

Recently, Kennedy et al., 1999, Science 283: 1544–1548 showed that protein tyrosine phosphatase PTP-1B is a negative regulator of the insulin signalling pathway, suggesting that inhibitors of this enzyme may be beneficial in the treatment of Type 2 diabetes. Mice lacking PTP-1B are resistant to both diabetes and obesity.

Thus, inhibitors of PTP-1B improve insulin-sensitivity. They have utility in controlling or treating Type 1 and Type 2 diabetes, in improving glucose tolerance, and in improving insulin sensitivity in patients in need thereof. The compounds may also be useful in treating or preventing cancer, neurodegenerative diseases and the like.

SUMMARY OF THE INVENTION

Compounds represented by formula I, including pharmaceutically acceptable salts thereof, and prodrugs thereof, are PTP-1B inhibitors that are useful in the treatment of diabetes and related medical conditions.

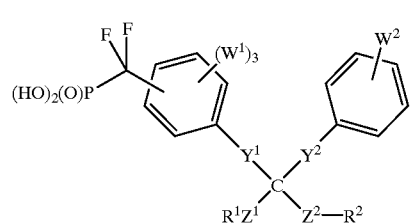

I

In compounds of Formula I, $R^1$ is phenyl or $C_{1-6}$ alkyl, wherein said $R^1$ is optionally substituted with 1–7 substituents independently selected from —C(O)OH, $SC_{1-3}$alkyl, CN, halogen, —C(O)O$C_{1-6}$alkyl$(R^c)_{0-3}$, —C(O)N$R^aR^b$, O$C_{1-6}$alkyl$(R^c)_{0-3}$, $C_{1-6}$alkyl$(R^c)_{0-3}$, C(O)$C_{1-6}$alkyl$(R^c)_{0-3}$, —NHC(O)$C_{1-4}$alkyl$(R^c)_{0-3}$, NHC(O)NH$C_{1-4}$alkyl$(R^c)_{0-3}$, —NHC(O)NH—Ar, and Het, wherein Ar is phenyl, and wherein Het is a five-membered heteroaryl comprising 1–4 heteroatoms selected from 0–4 nitrogen atoms, 0–1 oxygen atoms, and 0–1 sulfur atoms, where the heteroaryl also optionally comprises 0–2 carbonyl groups in the ring, and Ar and Het are each optionally substituted with 1–3 substituents independently selected from halogen, $C_{1-3}$alkyl, $C_{1-3}$fluoroalkyl, O$C_{1-3}$alkyl, and O$C_{1-3}$fluoroalkyl;

$R^a$ and $R^b$ are each independently selected from the group consisting of H and $C_{1-4}$alkyl;

Each $R^c$ is independently selected from a group consisting of OH, O$C_{1-3}$alkyl, O$C_{1-3}$haloalkyl, $C_{0-6}$alkylene $CO_2H$, Aryl, and Aryl substituted with 1–3 substituents independently selected from halogen, $C_{1-4}$alkyl, $C_{1-4}$haloalkyl, O$C_{1-4}$alkyl, and O$C_{1-4}$haloalkyl;

$R^2$ is 1H-1,2,3-benzotriazol-1-yl, pyridinyl, or phenyl, $R^2$ being optionally substituted with 1–3 halogens;

$Z^1$ is a bond;

$Z^2$ is —C(O)—, S, SO, $SO_2$, $CH_2$, or a bond;

$Y^1$ and $Y^2$ are each a bond or an aliphatic linear or branched hydrocarbon residue having from 1–8 carbon atoms and 0–4 double bonds, optionally also including a cycloalkyl group having 3–6 carbon atoms;

each $W^1$ is independently selected from H and halogen;

$W^2$ is selected from the group consisting of H, —OCF$_2$CO$_2$H, —CF$_2$PO$_3$H$_2$, —C(O)O$C_{1-6}$ alkyl, and Ar, wherein Ar is optionally substituted with 1–3 substituents independently selected from halogen, $C_{1-3}$ alkyl, $C_{1-3}$ fluoroalkyl, O$C_{1-3}$ alkyl, and —O$C_{1-3}$ fluoroalkyl;

with the proviso that when all $W^1$ groups are H, $R^1$ is phenyl, $R^2$ is phenyl or 1H-1,2,3-benzotriazol-1-yl, and $Y^1$ and $Y^2$ are $CH_2$, then one or both of $R^1$ and $R^2$ are substituted, and $R^1$, if substituted, is substituted with a substituent other than fluorine or —SCH$_3$.

Methods of treating, controlling, or preventing diabetes, obesity and other related disease and conditions, using the compounds of Formula I are disclosed herein. Pharmaceutical compositions and combination therapies are also disclosed.

DETAILED DESCRIPTION OF THE INVENTION

In a subset of compounds of Formula I as recited above,
$Y_1$ is —$CH_2$—,
$Y^2$ is $C_{1-3}$alkylene or $C_{1-3}$alkenylene;
and $R^1$, $R^2$, $Z^1$, $Z^2$, $W^1$, $W^2$, $R^a$, $R^b$, $R^c$, and any provisos are as previously defined.

In another subset of compounds of Formula I:
$R^1$ is phenyl which is optionally substituted with one substituent selected from —C(O)OH, —C(O)O$C_{1-4}$alkyl, —NHC(O)NH—$C_6H_3(CH_3)_2$, and —C(O)NR$^a$R$^b$, wherein R$^a$ and R$^b$ are each independently selected from H and $C_{1-4}$alkyl;
$R^2$ is 1H-1,2,3-benzotriazol-1-yl or phenyl which is optionally substituted with one halogen;
$Y^1$ is $CH_2$;
$Y^2$ is —$CH_2CH=CH_2$— or —$CH_2$—;
$W^2$ is selected from the group consisting of H, —OCF$_2$C(O)OH, —CF$_2$PO$_3$H$_2$, and —C(O)OCH$_3$;
and $Z^1$, $Z^2$, $W^1$, $R^a$, $R^b$, $R^c$, and any provisos are as defined above.

Another group of compounds of Formula I is defined as follows:
$R^1$ is phenyl which is optionally substituted with —C(O)O$C_{1-4}$alkyl;
$R^2$ is phenyl which is optionally substituted with one halogen;
$Z^1$ is a bond;
$Z^2$ is —C(O)—;
$Y^1$ is —$CH_2$—;
$Y^2$ is —$CH_2CH=CH_2$—;
$W^1$ is H or a single halogen on the aromatic ring in a position adjacent to —CF$_2$PO$_3$H$_2$; and
$W^2$ is H.

In another embodiment of this invention,
$R^1$ is phenyl which is optionally substituted with one substituent selected from (1) —C(O)O—$C_{1-4}$alkyl, (2) —NHC(O)NH-aryl, where aryl is phenyl which is optionally substituted with 1–3 substituents independently selected from $C_{1-3}$alkyl and halogen, and (3) —C(O)NR$^a$R$^b$, wherein R$^a$ and R$^b$ are each independently selected from H and $C_{1-3}$alkyl;
$R^2$ is phenyl which is optionally substituted with one halogen;
$Z^1$ is a bond;
$Z^2$ is —C(O)—;
$Y^1$ is —$CH_2$—;
$Y^2$ is —$CH_2$— or a bond;
$W^1$ is H or a halogen atom on the aromatic ring in a position adjacent to —CF$_2$PO$_3$H$_2$; and
$W^2$ and any provisos are as defined in Claim 1.

Finally, specific compounds of Formula I are provided in Table 1, Table 2 and Examples 1–43.

Methods of treating, preventing, or controlling diabetes and other diseases using the compounds of Formula I are disclosed herein. A method of treating, controlling or preventing diabetes and complications thereof in a mammalian patient in need of such treatment includes the administration to the patient an anti-diabetic effective amount of a compound of Formula I. A method of treating, controlling or preventing obesity in a mammalian patient in need of such treatment comprises the administration to the patient an anti-obesity effective amount of a compound in accordance with claim 1. Such methods also include the administration of a second compound, which may be an anti-diabetic compound, an anti-obesity compound, or an HMG-CoA reductase inhibitor, in an amount effective to treat, control or prevent diabetes or obesity, or to improve a poor lipid profile.

A method of treating, controlling or preventing atherosclerosis in a mammalian patient in need of such treatment comprises administering to the patient an effective amount of a compound of Formula I and an effective amount of an HMG-CoA reductase inhibitor.

More generally, compounds of Formula I may be used as the active compound in a method for treating, preventing, or controlling one or more diseases or conditions selected from Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease. The method comprises the administration of an effective amount of the compound of Formula I. Combination treatments can also be used in which case, the method comprises the administration of a compound of Formula I and an effective amount of one or more pharmaceutically active compounds selected from the group consisting of an HMG-CoA reductase inhibitor, an anti-obesity agent, and an antidiabetic compound.

Pharmaceutical compositions also can be made using the compounds of Formula I. Compositions that are suitable for the treatment, prevention or control of one or more diseases or conditions selected from Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease contain an effective amount of a compound of Formula I in combination with a pharmaceutically acceptable carrier.

Such pharmaceutical compositions may also include a second anti-diabetic agent or an anti-obesity agent. They may also include a cholesterol lowering agent. Pharmaceutical compositions may therefore include: (1) an effective amount of a compound of Formula I, (2) an effective amount of one or more pharmaceutically active compounds selected from the group consisting of an HMG-CoA reductase inhibitor, an anti-obesity agent, and an anti-diabetic agent, and (3) a pharmaceutically acceptable carrier.

Such pharmaceutical compositions that contain a second active compound or composition and that are suitable for the treatment, prevention or control of one or more diseases or conditions selected from the group consisting of Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease, may be comprised of the following:
(1) an effective amount of a compound of Formula 1;
(2) an effective amount of one or more pharmaceutically active compounds listed below; and (3) a pharmaceutically acceptable carrier; where the pharmaceutically active compounds are selected from the group consisting of:
  (a) insulin sensitizers including (i) PPAR-gamma agonists such as the glitazones (e.g. troglitazone, pioglitazone, englitazone, MCC-555, rosiglitazone, and the like), and compounds disclosed in WO97/27857, 97/28115, 97/28137 and 97/27847; (ii) biguanides such as metformin and phenformin;
  (b) insulin or insulin mimetics;
  (c) sulfonylureas such as tolbutamide and glipizide, or related materials;
  (d) alpha-glucosidase inhibitors (such as acarbose);
  (e) cholesterol lowering agents such as (i) HMG-CoA reductase inhibitors (lovastatin, simvastatin and pravastatin, fluvastatin, atorvastatin, rivastatin and other statins), (ii) sequestrants (cholestyramine, colestipol and dialkylaminoalkyl derivatives of a cross-linked dextran), (iii) nicotinyl alcohol, nicotinic acid or a salt thereof, (iv) PPAR-alpha agonists such as fenofibric acid derivatives (gemfibrozil, clofibrate, fenofibrate and bezafibrate), (v) inhibitors of cholesterol absorption including beta-sitosterol and acyl CoA:cholesterol acyltransferase inhibitors, such as for example melinamide, and (vi) probucol;
  (f) PPAR-alpha/gamma agonists;
  (g) antiobesity compounds such as appetite suppressants, fenfluramine, dexfenfluramine, phentiramine, sulbitramine, orlistat, neuropeptide Y5 inhibitors (NP Y5 receptor antagonosts), leptin, which is a peptidic hormone, beta-3 adrenergic receptor agonists, and PPARγ antagonists and partial agonists;
  (h) ileal bile acid transporter inhibitors; and
  (i) insulin receptor activators.

Abbreviations

The following abbreviations have the indicated meanings:
Ac=acetyl
AIBN=2.2-azobisisobutyronitrile
Bn=benzyl
Bz=benzoyl
DAST=diethylamino sulfur trifluoride
DBU=diazabicyclo[5.4.0]undec-7-ene
DIBAL-H=diisobutylaluminum hydride
DMAP=4-(dimethylamino)pyridine
DMF=N,N-dimethylformamide
DMSO=dimethyl sulfoxide
Et₃N=triethylamine
HBSS=Hanks balanced salt solution
KHMDS=potassium hexamethyldisilazide
KOtBu=potassium tert-butoxide
LDA=lithium disopropylamide
LHMDS=lithium hexamethyldisilazide
LPS=lipopolysaccharide
mCPBA=metachloro perbenzoic acid
MMPP=magnesium monoperoxyphthalate
Ms=methanesulfonyl=mesyl
MsO=methanesulfonate=mesylate
NBS=N-bromosuccinimide
NCS=N-chlorosuccinimide
NIS=N-iodosuccinimide
Oxone®=potassium peroxymonosulfate
PCC=pyridinium chlorochromate
PDC=pyridinium dichromate
PPA=polyphosphoric acid
PTP=protein tyrosine phosphatase
r.t.=room temperature
rac.=racemic
Tf=trifluoromethanesulfonyl=triflyl
TFA=trifluoroacetic acid
TFAA=trifluoroacetic anhydride
TfO=trifluoromethanesulfonate=triflate
THF=tetrahydrofuran
TLC=thin layer chromatography
Ts=p-toluenesulfonyl=tosyl
TsO=p-toluenesulfonate=tosylate
Tz=1H (or 2H)-tetrazol-5-yl Alkyl Group Abbreviations
  Me=methyl
  Et=ethyl
  n-Pr=normal propyl
  i-Pr=isopropyl
  n-Bu=normal butyl
  i-Bu=isobutyl
  s-Bu=secondary butyl
  t-Bu=tertiary butyl
  c-Pr=cyclopropyl
  c-Bu=cyclobutyl
  c-Pen=cyclopentyl
  c-Hex=cyclohexyl Dose Abbreviations
  bid=bis in die=twice daily
  qid=quater in die=four times a day
  tid=ter in die=three times a day Alkyl means linear, branched and cyclic structures, and combinations thereof, containing the indicated number of carbon atoms. Examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl-4-propylnonyl, cyclopropyl, cyclopentyl, cycloheptyl, adamantyl, cyclododecylmethyl, 2-ethyl-1-bicyclo[4.4.0] decyl and the like.

Fluoroalkyl means alkyl groups of the indicated number of carbon atoms in which one or more hydrogens is replaced by fluorine. Examples are —$CF_3$, —$CH_2CH_2F$, —$CH_2CF_3$, c-Pr—$F_5$, c-Hex-$F_{11}$ and the like. Haloalkyl has the analogous meaning for replacement of one or more hydrogen atoms with any halogen (Cl, Br, F, and/or I).

Alkenyl means linear, branched and cyclic structures, and combinations thereof containing a double bond with the indicated number of carbon atoms. Examples of alkenyl groups include allyl, 2-butenyl, 3-butenyl, 2-pentenyl, 2-cyclopentenyl, 3-cyclopentenyl, 2-methyl-cyclohexenyl, 2-cyclohexenyl, 3-cyclohexenyl and the like. Alkadienyl means the diunsaturated counterpart to alkenyl.

Alkynyl means linear, branched and cyclic structures, and combinations thereof containing a triple bond with the indicated number of carbon atoms. Examples of alkynyl groups include propargyl, 2-butynyl, 3-butynyl, 2-pentynyl, cyclopropylethynyl, and the like.

Alkylene, alkenylene, alkynylene, fluoroalkylene, alkadienylene, and the like, where the suffix "ene" has been added to the name of the monovalent radicals alkyl, alkenyl, alkynyl, fluoroalkyl, alkadienyl, and the like, describe divalent radicals that are the same as their monovalent counterparts, except that two hydrogen atoms rather than one are removed so that the radical will have two attachments.

Aryl means a 6–14 membered carbocyclic aromatic ring system comprising 1–3 phenyl rings. If two or more aromatic rings are present, then the rings are fused together, so that adjacent rings share a common side.

Heteroaryl (Het) as used herein represents a 5–10 membered aromatic ring system containing one ring or two fused rings, 1–4 heteroatoms, 0–4 of which are N atoms and 0–2 of which are O or $S(O)_y$ wherein y is as previously defined, and 0–2 carbonyl groups. Carbonyl groups, when present, are not counted as heteroatoms. Het includes, but is not limited to, furanyl, diazinyl, imidazolyl, isooxazolyl, isothiazolyl, oxadiazolyl, oxazolyl, pyrazolyl, pyridyl, pyrrolyl, tetrazinyl, thiazolyl, thienyl, triazinyl, triazolyl, 1H-pyrrole-2,5-dionyl, 2-pyrone, 4-pyrone, pyrrolopyridine, furopyridine and thienopyridine.

Benzoheteroaryl, which is a subset of Het includes aromatic ring systems containing one or more heteroatoms which also have a fused 6-membered benzene ring, such as 2H-1-benzopyran-2-one, 4H-1-benzopyran-4-one, 2(3H)benzofuranone, 3(2H)benzofuranone, 2,3-dihydrobenzofuran, 2,3-dihydrobenzothiophene, indole, benzofuran, benzothiophene, benzimidazole, benzoxazole, benzothiazole, benzotriazole, benzothiadiazole, 1H-isoindole-1,3(2H)-dione, quinoline, and isoquinoline.

Another subset of heteroaryls includes 5-membered heteroaryls, such as the following:

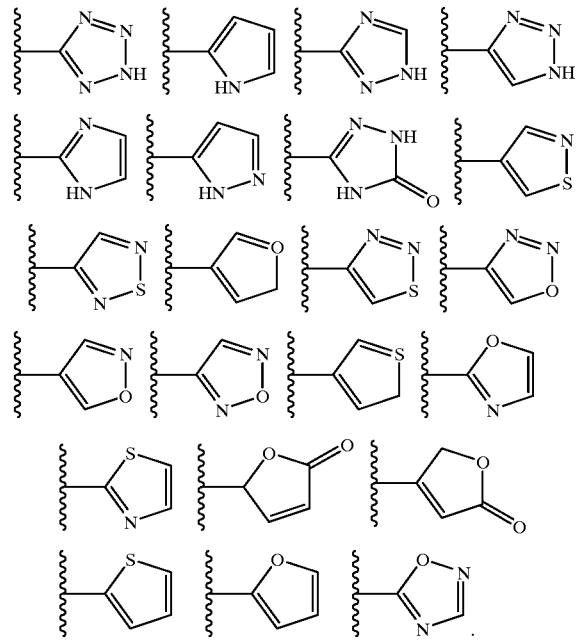

When a heteroaromatic ring is specified as optionally having one or more heteroatoms, this means that at least one heteroatom is present, selected from O, S and N, and up to 4 such heteroatoms may be present, depending upon the size of the ring specified.

When a moiety is specified as being optionally substituted, then the same moiety may also remain unsubstituted, unless otherwise stated.

Finally, when a list of possible choices is provided for a given moiety, and the moiety is used in more than one position in a chemical formula, the selection of a choice for the moiety in each position is independent of other selections, unless the definition says otherwise.

Metabolites—Prodrugs

Metabolites of the compounds of this invention that are therapeutically active and that are described by formula I also are within the scope of the claimed invention, as are prodrugs, which are compounds that are converted to the claimed compounds or salts of the claimed compounds after they have been administered to a patient. A non-limiting example of a prodrug of the phosphonic acids of this invention would be a monoester or diester of one or more phosphonic acid groups, where the ester functionality has a structure that makes it easily hydrolyzed or metabolized after administration to a patient. Examples of such prodrugs are the compounds shown below, where R'=H or a $C_{1-6}$ alkyl group, and R"=$C_{1-6}$ alkyl group or —$OC_{1-6}$ alkyl group, where Q is the residue of the molecule that is attached to the —$CF_2PO_3H_2$ group in formula I. The alkyl groups and alkoxy groups may optionally be substituted with one or more substituents independently selected from 1–5 halogen atoms, a phenyl group, or a mixture of these. The phenyl group, if present, may optionally be substituted with 1–3 substituents independently selected from halogen, —$CH_3$, —$CF_3$, —$OCH_3$ and —$OCF_3$. In these compounds, and as defined in general throughout this application, the alkyl groups and the alkyl portions of Oalkyl groups may be linear or branched and may optionally be cycloalkyl or may include a cycloalkyl group in their structure. For examples of related prodrug structures, see D. N. Srinivasta et al., Bioorganic Chemistry 12, 118–129 (1984).

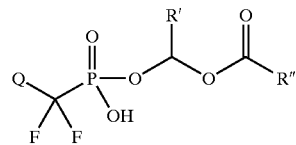

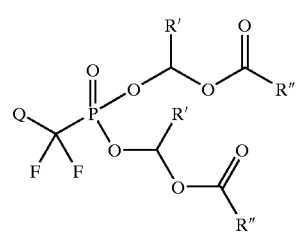

Other ester functionalities that may be used in the monoester or diester phosphonate prodrugs include phenyl esters and benzyl esters, where the phenyl ester groups have the structure —Ophenyl, and the benzyl ester groups have the structure —OCHR'phenyl, in which R' is H or $C_{1-6}$alkyl, and $C_{1-6}$alkyl is substituted as described above. In either case, phenyl is substituted as described above.

The prodrugs of this invention may therefore be defined as compounds having the formula Ia shown below:

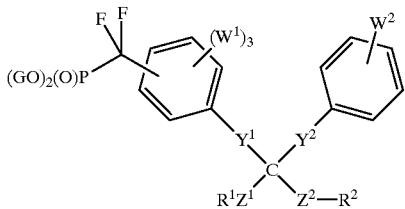

Ia

In the compounds having Formula Ia, $W^2$ is selected from the group consisting of H, —$OCF_2$ $C(O)OH$, —$CF_2PO(OG)_2$, —$C(O)OC_{1-6}alkyl$, and Ar, wherein Ar is as defined in Claim 1 and has the substituents defined in Claim 1, and all other substituent groups are as defined in Claim 1. At least one groups G is selected from phenyl, —CHR'phenyl, and —CHR'OC(=O)R", and the remaining groups G are selected from H, phenyl, —CHR'phenyl and —CHR'OC(=O)R", wherein each group R' is H or $C_{1-6}alkyl$ and each group R" is —$C_{1-6}alkyl$ or —$OC_{1-6}alkyl$, where $C_{1-6}alkyl$ and the alkyl portion of —$OC_{1-6}alkyl$ may optionally be substituted with one or more substituents independently selected from 1–5 halogen atoms, a phenyl group, or a mixture of these. The phenyl group in —CHR'phenyl, the phenyl group that is an optional substituent on $C_{1-6}alkyl$ and —$OC_{1-6}alkyl$, and the phenyl ester group that is obtained when G is phenyl may optionally be substituted with 1–3 groups independently selected from halogen, —$CH_3$, —$CF_3$, —$OCH_3$ and —$OCF_3$. By this definition, one of the phosphonic acid groups is a monoester or diester, and the other phosphonic acid group, if present, is a free acid or a monoester or diester.

In preferred compounds, the groups G that are not H are all the same because of the difficulty of synthesizing different G groups on the same phosphonates. In many cases, the prodrug will be a mixture of compounds having different levels of esterification on the phosphonic acid groups because of the difficulty of synthesizing a discrete pure compound.

Optical Isomers—Diastereomers—Geometric Isomers

Some of the compounds described herein contain one or more asymmetric centers, and these asymmetric centers may give rise to diastereomers and enantiomers, which may be in the form of enantiomeric or diastereomeric mixtures or of individual optical isomers. The present invention includes all such diastereomers and enantiomers, including racemic mixtures and resolved, enantiomerically pure forms, and pharmaceutically acceptable salts thereof. Some of the compounds described herein contain olefinic double bonds, and unless specified otherwise, include both E and Z geometric isomers.

Salts

The pharmaceutical compositions of the present invention comprise a compound of the current invention as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable acids; including inorganic and organic acids. Such acids include acetic, adipic, aspartic, 1,5-naphthalenedisulfonic, benzenesulfonic, benzoic, camphorsulfonic, citric, 1,2-ethanedisulfonic, ethanesulfonic, ethylenediaminetetraacetic, fumaric, glucoheptonic, gluconic, glutamic, hydriodic, hydrobromic, hydrochloric, isethionic, lactic, maleic, malic, mandelic, methanesulfonic, mucic, 2-naphthalenesulfonic, nitric, oxalic, pamoic, pantothenic, phosphoric, pivalic, propionic, salicylic, stearic, succinic, sulfuric, tartaric, p-toluenesulfonic acid, undecanoic, 10-undecenoic, and the like. Particularly preferred are citric, hydrobromic, hydrochloric, maleic, methanesulfonic, phosphoric, sulfuric and tartaric acids.

It will be understood that in the discussion of methods of treatment or of specific compounds which follows, references to the compounds of Formula I and other formulae are meant to include the pharmaceutically acceptable salts.

Utilities

Inhibitors of PTP-1B improve insulin-sensitivity and thus have utility in preventing or treating Type 1 and Type 2 diabetes, improving glucose tolerance and insulin-sensitivity when there is insulin-resistance, and in treating or preventing obesity, all in mammals that are in need of such treatments or that might benefit from such treatments. The compounds also exhibit a beneficial reduction in triglycerides and lipids. Compounds in the present class of phosphonic acids are advantageous over phosphonic acids previously investigated as candidate PTP-1B inhibitors. The compounds of this invention show greater selectivity for PTP-1B over T-Cell Protein Tyrosine Phosphatase (TCPTP) when compared with other phosphonates. This advantage minimizes possible toxicity due to the inhibition of TCPTP activity. Further, compounds in the present invention may be more potent inhibitors and may have improved pharmacokinetics when compared with other phosphonates. These compounds are also active in intact cell-based assays.

The PTP-1B inhibitors may also be useful in the treatment, prevention or control of a number of conditions that accompany type 2 diabetes, including hyperlipidemia, hypertriglyceridemia, hypercholesterolemia (including beneficially raising low HDL levels), atherosclerosis, vascular restenosis, pancreatitis, adipose cell tumors, adipose cell carcinomas such as liposarcoma, dyslipidemia, inflammatory bowel disease, inflammation in general, and other disorders where insulin resistance is a component. Finally, the compounds may be used to treat or prevent cancer, such as prostate cancer, neurodegenerative diseases and the like.

Pharmaceutical Compositions

For the treatment of any of these PTP-1B-mediated diseases the active compound may be administered orally, topically, parenterally, by inhalation spray or rectally in dosage units containing conventional pharmaceutically acceptable carriers. The term parenteral as used herein includes subcutaneous, intravenous, intramuscular and intrasternal injection and infusion techniques. In addition to the treatment of warm-blooded animals such as mice, rats, horses, cattle, sheep, dogs, cats, etc., the compounds of the invention are useful for the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxy-ethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical composition may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent, for example as a solution in 1,3-butanediol. Examples of vehicles and solvents include water, Ringer's solution and isotonic sodium chloride. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds may also be administered in the form of suppositories. These compositions can be prepared by mixing the drug with a suitable non-irritating excipient which is solid at ordinary temperatures but molten at the body temperature and will therefore release the drug. Such materials include cocoa butter and polyethylene glycols.

For topical use, creams, ointments, gels, solutions or suspensions containing the compound are employed. (For purposes of this application, topical application includes mouth washes and gargles.) Topical formulations may include cosolvents, emulsifiers, penetration enhancers, preservatives, emollients and the like.

The pharmaceutical composition may also be further comprised of a second anti-diabetic or anti-obesity effective compound.

Dose Ranges

Dosage levels on the order of from about 0.01 mg to about 100 mg/kg of body weight per day are useful in the treatment of the above-indicated conditions, or alternatively about 0.5 mg to about 7 g per patient per day. For example, the diseases and conditions described herein may be effectively treated by the administration of from about 0.01 to 50 mg of the compound per kilogram of body weight per day, or alternatively about 0.5 mg to about 3.5 g per patient per day.

The active ingredient is typically combined with the carrier to produce a dosage form suitable for the particular patient being treated and the particular mode of administration. For example, a formulation intended for the oral administration of humans may contain from about 0.5 mg to about 5 g of the active agent, compounded with an appropriate and convenient amount of carrier material which may vary from about 5 to about 95 percent of the total composition. Representative dosage forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It is understood that the specific dose level for any particular patient will depend upon a variety of factors including the age, body weight, general health, sex, diet, time of administration, route of administration, rate of excretion, drug combination and the severity of the particular disease undergoing therapy.

Combinations with Other Drugs

In further aspects, the invention encompasses pharmaceutical compositions for treating PTP-1B mediated diseases as defined above comprising an effective amount of the active compound and one or more other pharmaceutically active compounds, such as anti-diabetic compounds (for example, insulin, sulfonyl ureas, PPAR-alpha and/or -gamma ligands, including ligands that have both PPAR-alpha and -gamma activity), anti-obesity compounds, and compounds that improve the lipid profile of the patient.

Thus, the methods of treatment or prevention described herein may further be comprised of administering to said patient a second anti-diabetic compound in an amount effective to treat, control, or prevent diabetes, alone or in combination with the PTP-1B inhibitors of this invention.

Similarly, the methods of treatment or prevention described herein may further be comprised of administering to said patient an anti-obesity compound in an amount effective to treat, control or prevent obesity, alone orin combination with the PTP-1B inhibitors of this invention.

Similarly, the methods of treatment of diabetes may comprise the administration of a cholesterol biosynthesis inhibitor, particularly an HMG-CoA reductase inhibitor, such as lovastatin, simvastatin, pravastatin, fluvastatin, atorvastatin and rivastatin, in an amount effective to improve the lipid profile. In combination with a PTP-1B inhibitor, this may be beneficial in treating or preventing atherosclerosis and other conditions that often are associated with Type 2 diabetes.

Examples of other pharmaceutically active compounds that may be combined with a compound of Formula I and administered in combination with the PTP-1B inhibitors include, but are not limited to, the following compounds or compositions or groups of compounds or compositions that are used as anti-diabetes compounds (a, b, c, d, f, and i below), anti-obesity compounds (g below), and/or compounds or compositions for lipid profile control (e and h below):

(a) insulin sensitizers including (i) PPAR-gamma agonists such as the glitazones (e.g. troglitazone, pioglitazone, englitazone, MCC-555, rosiglitazone, and the like), and compounds disclosed in WO97/27857, 97/28115, 97/28137 and 97/27847; (ii) biguanides such as metformin and phenformin;

(b) insulin or insulin mimetics;

(c) sulfonylureas such as tolbutamide and glipizide, or related materials;

(d) alpha-glucosidase inhibitors (such as acarbose);

(e) cholesterol lowering agents such as (i) HMG-CoA reductase inhibitors (lovastatin, simvastatin and pravastatin, fluvastatin, atorvastatin, rivastatin and other statins), (ii) sequestrants (cholestyramine, colestipol and dialkylaminoalkyl derivatives of a cross-linked dextran), (iii) nicotinyl alcohol, nicotinic acid or a salt thereof, (iv) PPAR-alpha agonists such as fenofibric acid derivatives (gemfibrozil, clofibrate, fenofibrate and bezafibrate), (v) inhibitors of cholesterol absorption including beta-sitosterol and acyl CoA:cholesterol acyltransferase inhibitors such as melinamide, and (vi) probucol;

(f) PPAR-alpha/gamma agonists;

(g) antiobesity compounds such as appetite suppressants, fenfluramine, dexfenfluramine, phentiramine, sulbitramine, orlistat, neuropeptide Y5 inhibitors (NP Y5 receptor antagonosts), leptin, which is a peptidic hormone, beta-3 adrenergic receptor agonists, and PPARγ antagonists and partial agonists;

(h) ileal bile acid transporter inhibitors; and (i) insulin receptor activators, such as those disclosed in copending, commonly assigned U.S. application Ser. Nos. 09/095,244 and 09/280,602.

Where a second pharmaceutical is used in addition to an active compound taught herein, the two pharmaceuticals may be administered together in a single composition, separately at approximately the same time, or on separate dosing schedules. The important feature is that their dosing schedules comprise a treatment plan in which the dosing schedules overlap in time and thus are being followed concurrently.

Methods of Synthesis

The compounds of the present invention can be prepared according to the following methods.

Method A-1

Toluic acid derivative 1 can be treated with NBS in 1,2-dichloroethane with AIBN under light at reflux to give bromide 2. The acid can be reduced with borane in THF to provide the alcohol 3 which in turn is oxidized with $MnO_2$ to afford aldehyde 4. Di-tert-butyl phosphite can be deprotonated with a base such as LHMDS and reacted with aldehyde 4. The resulting alcohol 5 is then oxidized with $MnO_2$ to provide ketone 6. The ketone 6 is treated with DAST to afford compound 7.

Method A-1

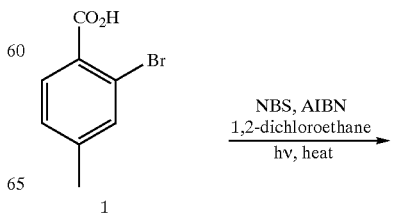

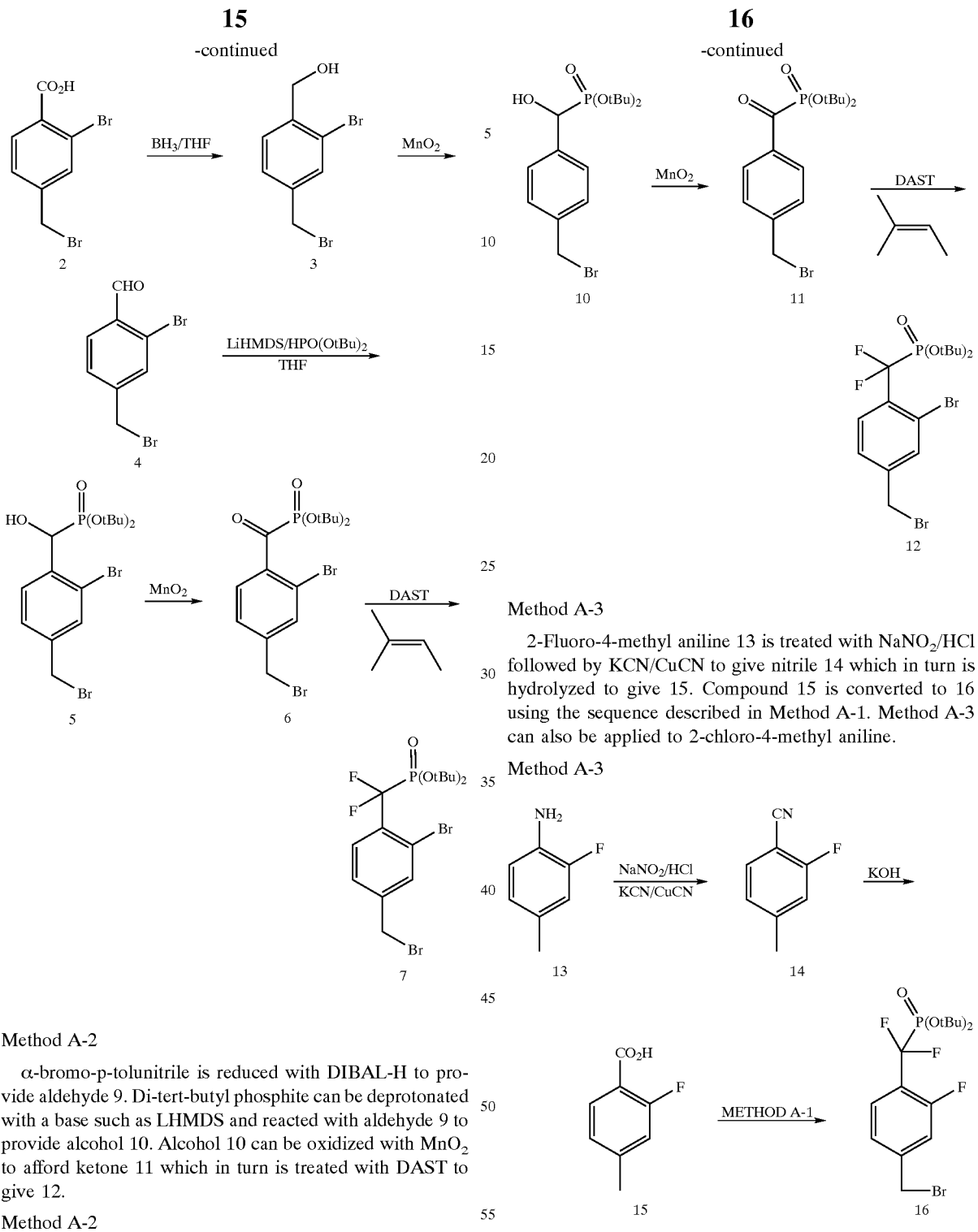

Method A-2

α-bromo-p-tolunitrile is reduced with DIBAL-H to provide aldehyde 9. Di-tert-butyl phosphite can be deprotonated with a base such as LHMDS and reacted with aldehyde 9 to provide alcohol 10. Alcohol 10 can be oxidized with $MnO_2$ to afford ketone 11 which in turn is treated with DAST to give 12.

Method A-2

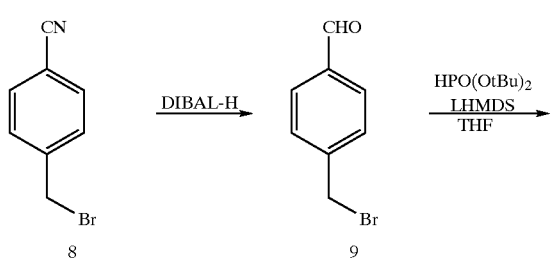

Method A-3

2-Fluoro-4-methyl aniline 13 is treated with $NaNO_2/HCl$ followed by KCN/CuCN to give nitrile 14 which in turn is hydrolyzed to give 15. Compound 15 is converted to 16 using the sequence described in Method A-1. Method A-3 can also be applied to 2-chloro-4-methyl aniline.

Method A-3

Method A-4

The methyl ester of 4-Aminobenzoic Acid II can be brominated with pyridinium tribromide to give III, which is treated with $NaNO_2/HCl$ and KCN/CuCN to give nitrile IV. DIBAL reduction followed by bromination with $POBr_3$, gives VI, which is treated with lithium dialkyl phosphite to afford the phosphonate alcohol VII. Swern oxidation followed by fluorination with DAST provides the desired difluoromethyl phosphonate IX.

Method A-4

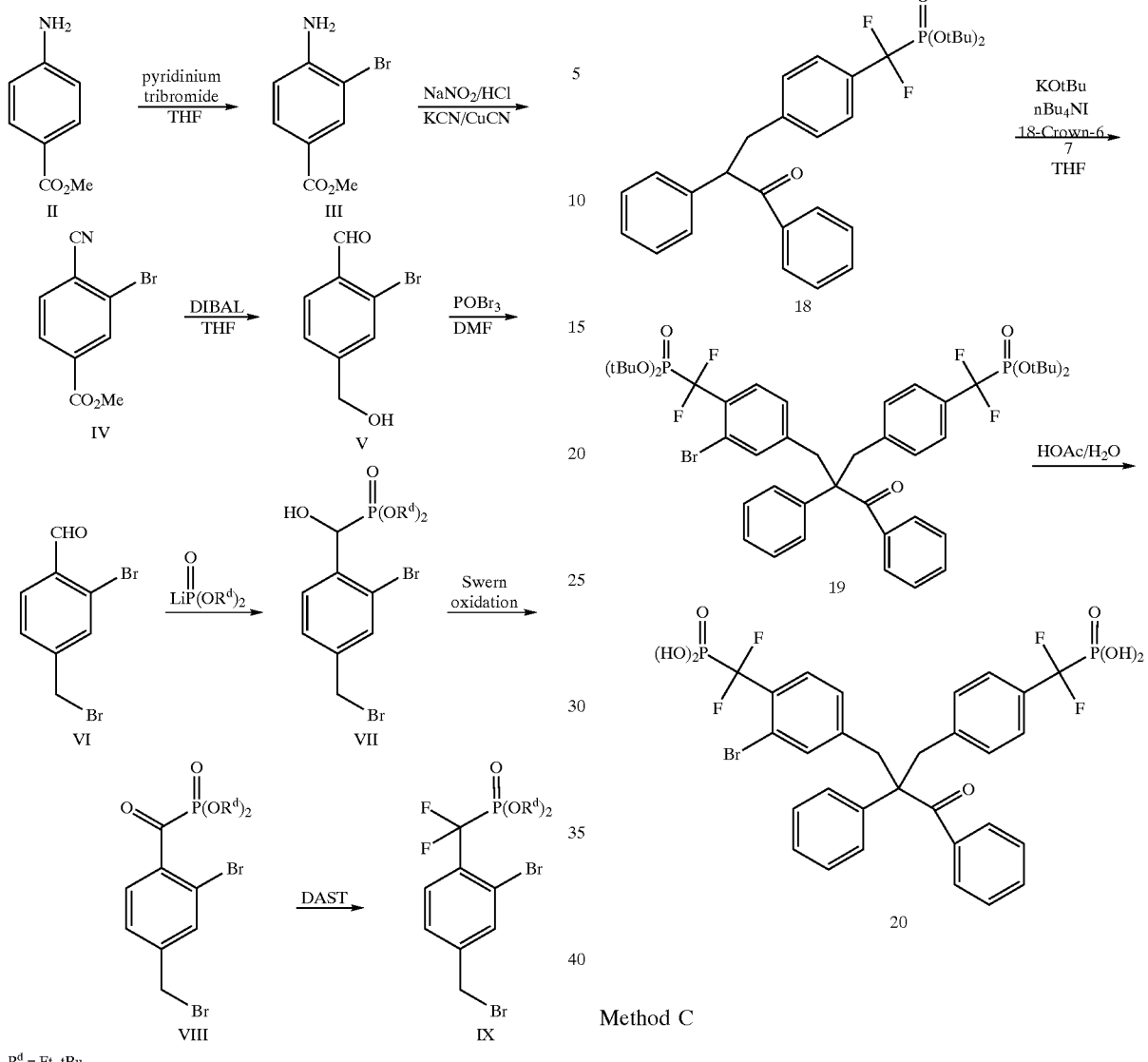

$R^d$ = Et, tBu

Method B

Deoxybenzoin 17 can be deprotonated with a base such as NaH or KOtBu and treated with compound 12 to give 18. Compound 18 can be alkylated a second time with 7 using a base such as KOtBu in the presence of $nBu_4NI$ and 18-Crown-6 to give 19. The ester is then hydrolyzed with $AcOH/H_2O$ to give acid 20.

Method B

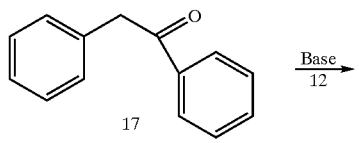

Method C

Template 21 is deprotonated with a suitable base such as NaH, KOtBu, LHMDS, nBuLi, s-BuLi, t-BuLi, LDA or a combination of these bases, and the resulting anion is alkylated with 22 in a suitable protected form such as the tBu ester in the case of an acid-containing $W^2$. The resulting product 23 is treated with a suitable base and alkylated with 24 to yield 25, which after acid treatment yields the desired compound I. In cases where $Y^2$ includes a cyclopropane in its structure, the cyclopropyl is conveniently synthesized from the corresponding olefin by using cyclopropanation methods well known in the art.

Method C

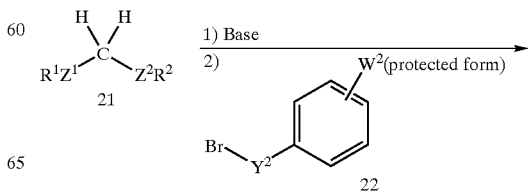

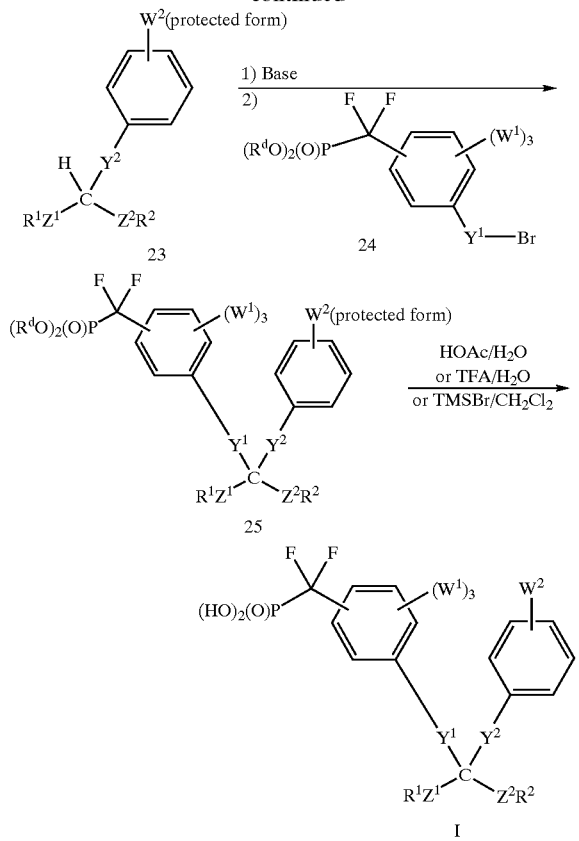

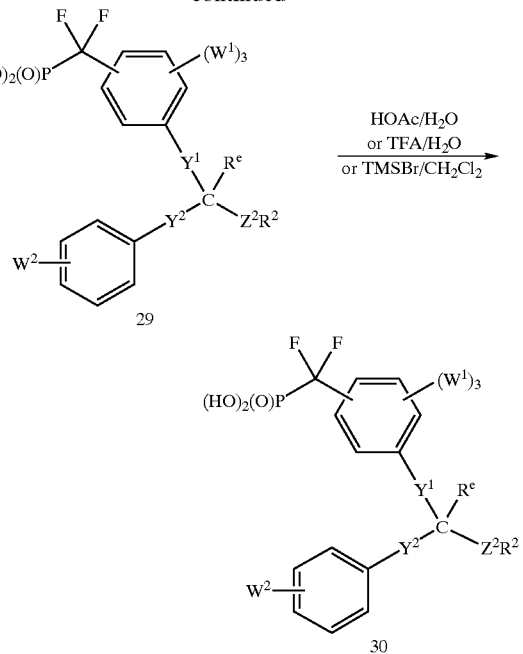

X = Halogen
Y² = a bond
W² ≠ OCF₃CO₂H, CF₂PO₃H
R^d = tBu, Et
R^e = C₁₋₆ alkyl, allyl Method E Benzaldehyde 31 is stirred overnight with TMSCN/ZnI₂ to give TMS cyanohydrin 32. Treatment of 32 with a base such as LHMDS followed by an alkylating agent 33 and nBu₄NF yields the desired deoxybenzoin 34.

Method E

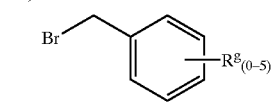

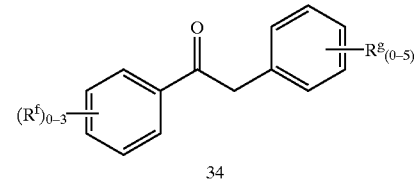

$R^f$ = halogen
$R^g$ = previously described substituents of $R^1$

Method D

Template 26 is deprotonated with a suitable base such as NaH, KOtBu, LHMDS, or nBuLi, and the anion is alkylated with an alkyl or allyl halide X-R^e to give 27. A second alkylation with 28 gives bisalkylated product 29, which upon acid treatment yields the desired compound 30.

Method D

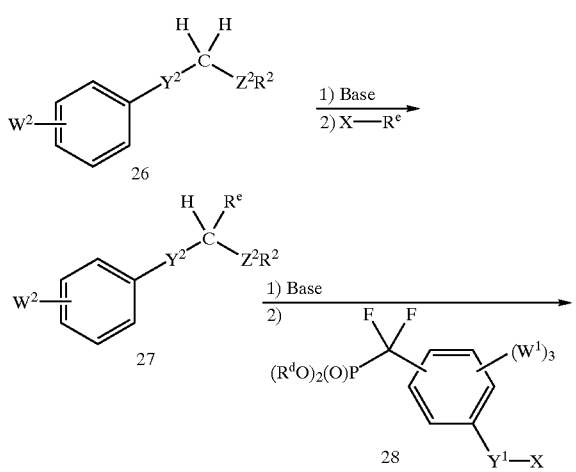

Method F

The disodium phosphonate 35 can be alkylated with a chloroalkyl ester (*Synth. Com.* 25(18) 2739 (1995)) or carbonate (*Antiviral Chemistry & Chemotherapy* 8, 557

(1997)) to give both the mono and diprotected phosphonates which can be separated by flash chromatography on silica gel. Q in Methods F, G and H is the residue of the compound described by Figure I that is attached to the —CF$_2$PO(OH)$_2$ group.

Method F

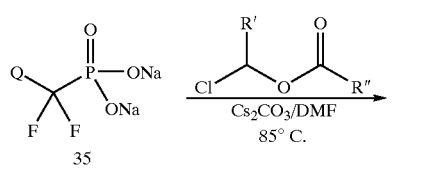
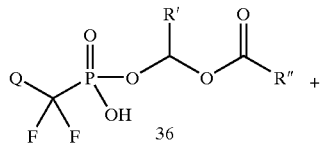
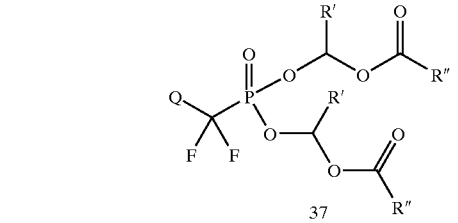

Method G

Phosphonic acid 38 can be treated with Cs$_2$CO$_3$ and a chloroalkyl ester or carbonate in CH$_3$CN to give a mixture of mono and diprotected phosphonates which can be separated by flash chromatography on silica gel.

Method G

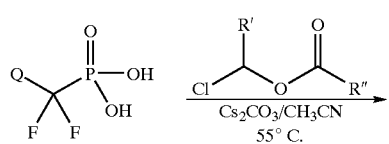
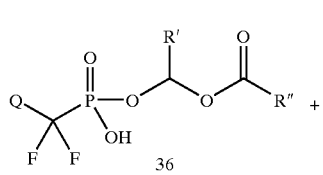
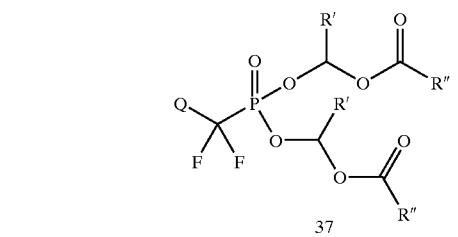

Method H

Phosphonic acid 38 can be treated with silver trifluoracetate to give the disilver salt 39 which can be treated with an iodoalkyl ester (*Eur. J. Phar. Sci.* 4, 49 (1996)) or carbonate to give a mixture of the mono and diprotected phosphonates which are separable by flash chromatography.

Method H

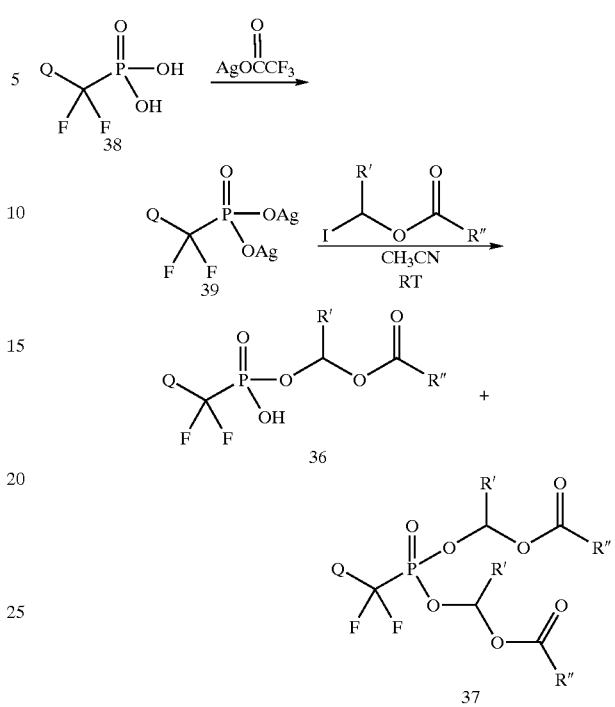

Method I

Pyridine carboxylic acid 40 can be treated with thionyl chloride, followed by N,O-dimethylhydroxylamine hydrochloride/pyridine to give the Wienreb amide 41. This intermediate can be reacted with a Grignard reagent such as 42 to give the desired template 43.

Method I

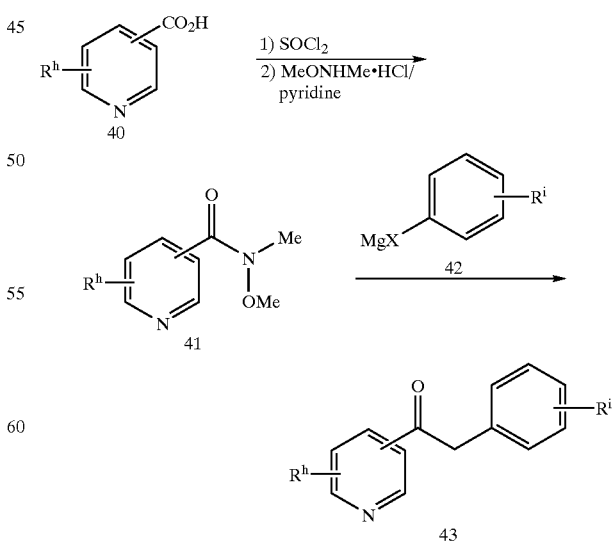

R$^h$ = halogen
R$^i$ = halogen, O-alkyl, S-alkyl

TABLE 1
Structures of Examples
| | Example | Method |
|---|---|---|
| 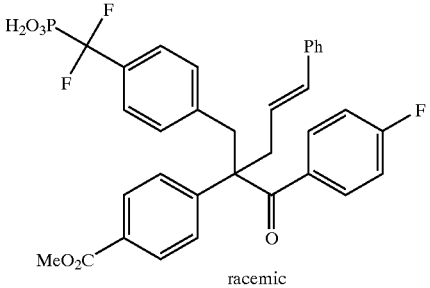 racemic | 1 | A-2 + E + C |
| 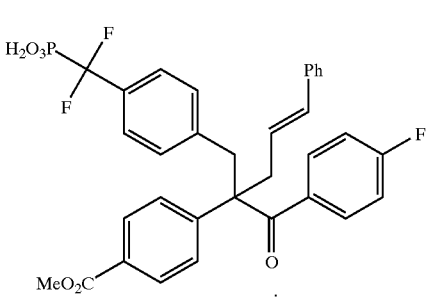 racemic | 1a, 1b | A-2 + E + C |
| enantiomers 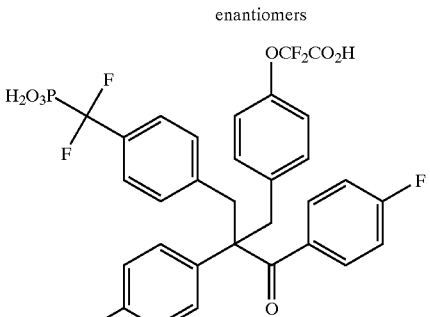 | 2 | A-2 + E + C |
| enantiomers 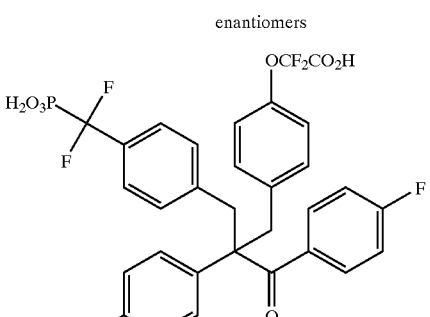 | 2a, 2b | A-2 + E + C |

TABLE 1-continued

Structures of Examples

| | Example | Method |
|---|---|---|
| enantiomers (structure) | 3 | A-2 + E + C |
| (structure) | 4 | A-2 + E + C |
| (structure) | 5 | A-2 + E + C |
| (structure) | 6 | A-2 + E + C |

TABLE 1-continued

Structures of Examples

| Structure | Example | Method |
|---|---|---|
| (structure 7) | 7 | A-2 + E + C |
| (structure 8) | 8 | A-2 + E + C |
| (structure 9, racemic) | 9 | A-2 + C |
| (structure 9a/9b, racemic) | 9a, 9b | A-2 + C |

TABLE 1-continued

Structures of Examples

| | Example | Method |
|---|---|---|
| enantiomers | 10 | A-2 + E + C |
| | 11 | A-2 + E + C |
| | 12 | A-2 + E + C |
| | 13 | A-2 + E + C |

TABLE 1-continued

Structures of Examples

| Example | Method |
|---------|--------|
| 14 | A-2 + C |
| 15 | A-2 + E + C |
| 16a | A-2 + E + C |
| 16b | A-2 + E + C |

(enantiomer for 16a and 16b)

TABLE 1-continued

Structures of Examples

| Example | Method |
|---------|--------|
| 17 | A-2 + E + C |
| 18 | A-1 + E + C |
| 19 | A-1 + D |
| 20 | A-1 + C |

TABLE 1-continued

Structures of Examples

| Structure | Example | Method |
|-----------|---------|--------|
| (structure with two F₂C-PO₃H₂ groups on aryl rings, one aryl bearing Br, central carbon with phenyl and benzoyl substituents) | 21 | A-1 + A-2 + C |
| (structure with two F₂C-PO₃H₂ groups on aryl rings, one aryl bearing Br, central carbon with phenyl and benzotriazolyl substituents) | 22 | A-1 + A-2 + C |
| (structure with two F₂C-PO₃H₂ groups on aryl rings, central carbon with 4-(MeO₂C)phenyl and benzotriazolyl substituents) | 23 | A-2 + C |

TABLE 1-continued

Structures of Examples

| Example | Method |
|---|---|
| 24 | A-2 + C |
| 25 | A-2 + C |
| 26 | A-3 + C |
| Ex. 27 | A-1 + C |

TABLE 1-continued

Structures of Examples

| Example | Method |
|---------|--------|
| Ex. 28 | A-1 + C |
| Ex. 29 | A-2 + C |
| Ex. 30 | A-2 + E + C |
| Ex. 31 | A-2 + E + C |

TABLE 1-continued

Structures of Examples

| Example | Method |
|---------|--------|
| Ex. 32 | A-2 + C |
| Ex. 33 | A-2 + E + C |
| Ex. 34 | A-2 + C |
| Ex. 35 | A-2 + C |

TABLE 1-continued

Structures of Examples

| Example | Method |
|---|---|
| Ex. 36 | A-2 + C |
| Ex. 37 | A-2 + E + C |
| Ex. 38 | A-2 + E + C |
| Ex. 39 | A-3 + D |

TABLE 1-continued

Structures of Examples

| Example | Method |
|---------|--------|
| Ex. 40 | A-1 + C + H |
| Ex. 41 | A-1 + C + G |
| Ex. 42 | A-1 + A-2 + C + G |

TABLE 1-continued

Structures of Examples

| Example | Method |
|---------|--------|
| Ex. 43 | A-1 + A-2 + C + G |

TABLE 2

Other Structures of the Invention

Assays for Demonstrating Biological Activity

Activity in the compounds of this application is demonstrated using the following assays for PTP-1B-inhibiting activity.

Phosphatase Assay Protocol

Materials

EDTA—ethylenediaminetetraacetic acid (Sigma)

DMH—N,N'-dimethyl-N,N'-bis(mercaptoacetyl)-hydrazine (synthesis published in *J. Org. Chem.* 56, pp. 2332–2337, (1991) by R. Singh and G. M. Whitesides and can be substituted with DTT-dithiothreitol Bistris-2,2-bis(hydroxymethyl)2,2',2"-nitrilotriethanol- (Sigma) Triton X-100-octylphenolpoly(ethyleneglycolether) 10 (Pierce)

Antibody: Anti-glutathione S-transferase rabbit (H and L) fraction (Molecular Probes)

Enzyme: Human recombinant PTP-1B, containing amino acids 1–320, fused to GST enzyme (glutathione S-transferase) or to FLAG peptide purified by affinity chromatography (Huyer et al, 1997, *J. Biol. Chem.*, 272, 843–852). Wild type contains active site cysteine (215), whereas mutant contains active site serine (215).

Tritiated peptide: Bz-NEJJ-CONH$_2$, Mwt. 808, empirical formula, $C_{32}H_{32}T_2O_{12}P_2F_4$

| Stock Solutions | |
|---|---|
| (10X) Assay Buffer | 500 mM Bistris (Sigma), pH 6.2, MW = 209.2 |
| | 20 mM EDTA (GIBCO/BRL) |
| | Store at 4° C. |
| Prepare fresh daily: | |
| Assay Buffer (1X) (room temp.) 2 mM EDTA | 50 mM Bistris |
| | 5 mM DMH (MW = 208) |
| Enzyme Dilution | |
| Buffer (keep on ice) | 50 mM Bistris |
| | 2 mM EDTA |
| | 5 mM DMH |
| | 20% Glycerol (Sigma) |
| | 0.01 mg/ml Triton X-100 (Pierce) |
| Antibody Dilution | |
| Buffer (keep on ice) | 50 mM Bistris |
| | 2 mM EDTA |

IC$_{50}$ Binding Assay Protocol:

Compounds (ligands) which potentially inhibit the binding of a radioactive ligand to the specific phosphatase are screened in a 96-well plate format as follows:

To each well is added the following solutions @ 25° C. in the following chronological order:

1. 110 μl of assay buffer.
2. 10 μl. of 50 nM tritiated BzN-EJJ-CONH$_2$ in assay buffer (1×) @ 25° C.
3. 10 μl. of testing compound in DMSO at 10 different concentrations in serial dilution (final DMSO, about 5% v/v) in duplicate @ 25° C.
4. 10 μl. of 3.75 μg/ml purified human recombinant GST-PTP-1B in enzyme dilution buffer.
5. The plate is shaken for 2 minutes.
6. 10 μl. of 0.3 μg/ml anti-glutathione S-transferase (anti-GST) rabbit IgG (Molecular Probes) diluted in antibody dilution buffer @ 25° C.

7. The plate is shaken for 2 minutes.
8. 50 μl. of protein A-PVT SPA beads (Amersham) @ 25° C.
9. The plate is shaken for 5 minutes. The binding signal is quantified on a Microbeta 96-well plate counter.
10. The non-specific signal is defined as the enzyme-ligand binding in the absence of anti-GST antibody.
11. 100% binding activity is defined as the enzyme-ligand binding in the presence of anti-GST antibody, but in the absence of the testing ligands with the non-specific binding subtracted.
12. Percentage of inhibition is calculated accordingly.
13. $IC_{50}$ value is approximated from the non-linear regression fit with the 4-parameter/multiple sites equation (described in: "Robust Statistics", New York, Wiley, by P. J. Huber (1981) and reported in nM units.
14. Test ligands (compounds) with larger than 90% inhibition at 10 μM are defined as actives.

Enzyme Assay PTP-1B
Assay buffer
    50 mM Bis-Tris (pH=6.3)
    2 mM EDTA
    5 mM N,N'-dimethyl-N,N'-bis(mercaptoacetyl)hydrazine (DMH)
Substrate
    10 mM fluorescein diphosphate (FDP) store at −20°C.
Enzyme dilution buffer
    50 mM Bis-Tris (pH=6.3)
    2 mM EDTA
    5 mM DMH
    20%(v/v) glycerol
    0.01% Triton X-100

The assay was carried out at room temperature in 96 well plates. The reaction mixture in 170 μl contained 50 mM Bis-Tris (pH=6.3), 2 mM EDTA, 5 mM N,N'-dimethyl-N,N'bis(mercaptoacetyl)hydrazine (DMH) and 10 μM fluorescein diphosphare (FDP). 10 μl of 10 concentrations (serial dilution) of the test compound (inhibitor) dissolved in DMSO or DMSO alone for control was added to each well and the plate was mixed for 2 min. The reaction was initiated by adding 20 μl of diluted PTP-1B (50 nM in 50 mM Bis/Tris (pH=6.3), 2 mM EDTA, 5 mM DMH, 20% glycerol and 0.01% Triton X-100. The phosphatase activity was followed by monitoring the appearance of the fluorescent product fluorescein monophosphate (FMP) continuously for 15–30 min, using the Cytofluor II plate reader (PerSeptive Biosystems Inc.) with excitation of 440 nm (slit width 20 nm) and emission at 530 nm (slit width 25 nm). All the assays were done at least in duplicate. The initial rate of FMP formation is plotted against the concentration of inhibitor and the data was fitted to 4-parameter equation and the inflection point of the fit is the $IC_{50}$.

Pharmacokinetics in Rats
Per Os Pharmacokinetics in Rats
Procedure

The animals are housed, fed and cared for according to the Guidelines of the Canadian Council on Animal Care.

Male Sprague Dawley rats (325–375 g) are fasted overnight prior to each PO blood level study.

The rats are placed in the restrainer one at a time and the box firmly secured. The zero blood sample is obtained by nicking a small (1 mm or less) piece off the tip of the tail. The tail is then stroked with a firm but gentle motion from the top to the bottom to milk out the blood. Approximately 1 mL of blood is collected into a heparinized vacutainer tube.

Compounds are prepared as required, in a standard dosing volume of 10 mL/kg, and administered orally by passing a 16 gauge, 3" gavaging needle into the stomach.

Subsequent bleeds are taken in the same manner as the zero bleed except that there is no need to nick the tail again. The tail is cleaned with a piece of gauze and milked/stroked as described above into the appropriately labelled tubes.

Immediately after sampling, blood is centrifuged, separated, put into clearly marked vials and stored in a freezer until analysed.

Typical time points for determination of rat blood levels after PO dosing are:
    0, 15 min, 30 min, 1 h, 2 h, 4 h, 6 h After the 4 hr time point bleed, food is provided to the rats ad libitum. Water is provided at all times during the study.

Vehicles

The following vehicles may be used in PO rat blood level determinations:

| PEG 200/300/400: | restricted to 2 mL/kg |
| Methocel 0.5%–1.0%: | 10 mL/kg |
| Tween 80: | 10 mL/kg |

Compounds for PO blood levels can be in suspension form. For better dissolution, the solution can be placed in a sonicator for approximately 5 minutes.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv\,(\text{mg/kg})}{AUCiv}$$

The units of CL are mL/h·kg (milliliters per hour kilogram)

Intravenous Pharmacokinetics in Rats
Procedure

The animals are housed, fed and cared for according to the Guidelines of the Canadian Council on Animal Care.

Male Sprague Dawley (325–375 g) rats are placed in plastic shoe box cages with a suspended floor, cage top, water bottle and food.

The compound is prepared as required, in a standard dosing volume of 1 mL/kg.

Rats are bled for the zero blood sample and dosed under $CO_2$ sedation. The rats, one at a time, are placed in a primed $CO_2$ chamber and taken out as soon as they have lost their righting reflex. The rat is then placed on a restraining board, a nose cone with $CO_2$ delivery is placed over the muzzle and the rat restrained to the board with elastics. With the use of forceps and scissors, the jugular vein is exposed and the zero sample taken, followed by a measured dose of compound which is injected into the jugular vein. Light digital pressure is applied to the injection site, and the nose cone is removed. The time is noted. This constitutes the zero time point.

The 5 min bleed is taken by nicking a piece (1–2 mm) off the tip of the tail. The tail is then stroked with a firm but gentle motion from the top of the tail to the bottom to milk the blood out of the tail. Approximately 1 mL of blood is collected into a heparinized collection vial. Subsequent bleeds are taken in the same fashion, except that there is no need to nick the tail again. The tail is cleaned with a piece of gauze and bled, as described above, into the appropriate labelled tubes.

Typical time points for determination of rat blood levels after I.V. dosing are either:

0, 5 min, 15 min, 30 min, 1 h, 2 h, 6 h or 0, 5 min, 30 min, 1 h, 2 h, 4 h, 6 h.

Vehicles

The following vehicles may be used in IV rat blood level determinations:

| | |
|---|---|
| Dextrose: | 1 mL/kg |
| 2-Hydroxypropyl-b-cyclodextrin | 1 mL/kg |
| DMSO (dimethyl-sulfoxide): | Restricted to a dose volume of 0.1 mL per animal |
| PEG 200: | Not more than 60% mixed with 40% sterile water - 1 mL/kg |

With Dextrose, either sodium bicarbonate or sodium carbonate can be added if the solution is cloudy.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv \, (mg/kg)}{AUCiv}$$

The units of CL are mL/h·kg (milliliters per hour kilogram).

PTP 1B Intact Cell Assay

This assay is the subject of copending, commonly assigned U.S. Provisional Application No. 60/123,243, filed Mar. 8, 1999, which patent application is incorporated herein by reference, and was recently published in Cromlish, Wanda A., Paul Payette and Brian P. Kennedy (1999) *Biochem Pharmocol* 58: 1539–1546.

Construction of Recombinant Baculovirus Transfer Vectors and Insect Cells

Briefly, using the Bac-to-Bac Baculovirus Expression System (Gibco-BRL, Mississauga, Ontario, Canada) PTP 1B cDNA (obtained from Dr. R. L. Erikson, Harvard University, USA), is cloned into the pFASTBAC donor plasmid engineered to include a FLAG sequence at the 5' end of the cDNA (PTP1B-FL). The recombinant plasmid is transformed into competent DH10BAC *E. Coli* cells. Following transposition and antibiotic selection, the recombinant bacmid DNA is isolated from selected *E. Coli* colonies and used to transfect sf9 insect cells (Invitrogen, San Diego, Calif., U.S.A.). The sf9 cells are cultured in spinner flasks at 28° C. in Graces supplemented medium (Gibco-BRL, Mississauga, Ontario, Canada) with 10% heat-inactivated fetal bovine serum (Gibco-BRL) following the protocol of Summers and Smith (*A manual for Methods for Baculovirus Vectors and Insect Culture Procedures*(Bulletin No. 1555). Texas A & M University, Texas Agricultural Experiment Station, College Station, Tex., 1987).

Intact Cell Assay

Infected sf9 cells expressing PTP1B-FL and mock infected cells, are harvested at 29 hpi (hours post infection) by gentle centrifugation (Beckman GS-6R) at 460 rpm, (48 g) for 5 min. Cells are washed once in assay buffer (Hanks' solution buffered with 15 mM Hepes, pH 7.4, obtained from Sigma, St. Louis, Mo., U.S.A.) and recentrifuged at 300 rpm (21 g) for 10 min. The cells are then gently resuspended in assay buffer and examined using a hemacytometer for cell density and viability by trypan blue exclusion. Assays are performed using a Tomtec Quadra 96 pipeting robot, programmed to mix the cells gently after each addition. In 200 $\mu$L of assay buffer, $2 \times 10^5$ PTP expressing cells or mock infected cells are dispensed into each well of 96-well polypropylene plates and pre-incubated either with a test compound or DMSO vehicle (3 $\mu$L), for 15 min at 37° C. The pre-incubated cells are challenged with a final concentration of 10 mM pNPP (p-nitrophenyl phosphate, obtained from Sigma-Aldrich Canada Ltd., Oakville, Ontario) for 15 min, centrifuged at 4° C. and the amount of substrate hydrolysis is determined spectrophotometerically at $OD_{405}$.

Oral Glucose Tolerance Test

Oral glucose tolerance tests are done on conscious Zucker obese fa/fa rats or obese ob/ob mice (age 12 weeks or older). The animals are fasted for 16–18 hours before use for experiments. A test compound or a vehicle is given either intraperitoneally or orally 60 minutes before oral administration of a glucose solution at a dose of 2 g/kg body weight. Blood glucose levels are measured using a Medisense glucometer from tail bled samples taken at different time points before and after administration of glucose. A time curve of the blood glucose levels is generated and the area-under-the-curve (AUC) for 120 minutes is calculated (the time of glucose administration being time zero). Percent inhibition is determined using the AUC in the vehicle-control group as zero percent inhibition.

In separate studies, C57BL/6J mice are fed a high fat (35%) and high carbohydrate (36%) diet obtained from Bioserv (Frenchtown, N.J.) for 3 to 4 weeks, at which time the mice gained 50–100% of the baseline body weight. Oral glucose tolerance tests are done in the same manner as described above.

EXAMPLES

The invention is further illustrated by the following examples, which are provided to illustrate the invention and are not to be construed as limiting the invention in any way. The following experimental methods were generally followed, unless stated otherwise:

(i) all operations were carried out at room or ambient temperature, that is, at a temperature in the range 18–25° C., (ii) evaporation of solvent was carried out using a rotary evaporator under reduced pressure (600–4000 pascals: 4.5–30 mm. Hg) with a bath temperature of up to 60° C., (iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (□) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (liter(s)), mL (milliliters), g (gram (s)), mg (milligrams(s)), mol (moles), mmol (millimoles), eq (equivalent(s)).

Example 1

Difluoro(4-{(4E)-2-(4-fluorobenzoyl)-2-[4-(methoxycarbonyl)phenyl]-5-phenyl-4-pentenyl}phenyl)methylphosphonic acid Step 1 2-(4-fluorophenyl)-2-[(trimethylsilyl)oxy]acetonitrile To p-fluorobenzaldehyde (25 g, 201 mmol) in $CH_2Cl_2$ (200 mL) were added TMSCN (28.43 g, 282 mmol) and $ZnI_2$ (0.200 g). The reaction mixture was stirred at r.t. overnight and evaporated to dryness.

Step 2 methyl-4-[2-(4-fluorophenyl)-2-oxoethyl]benzoate

To 2-(4-fluorophenyl)-2-[(trimethylsilyl)oxy]acetonitrile (0.500 g, 2.24 mmol) in degassed THF (11 ml) at −78° C. was added LHMDS 1M in THF (2.4 ml). To the previous reaction mixture a solution of methyl 4-(bromomethyl) benzoate (0.513 g, 2.25 mmol) in THF (2 ml) was then added. After a period of 1 h at r.t., tetrabutylammonium fluoride solution 1 M in THF (2.23 ml) was added to the reaction mixture and stirred for 10 minutes. Water was added and the mixture was extracted with ethyl acetate. The organic phase was dried over sodium sulfate and evaporated to dryness. The residue was purified by flash chromatography using hexane/ethyl acetate 30% giving 0.4 g of the title compound.

Step 3 methyl 4-[(E)-1-(4-fluorobenzoyl)-4-phenyl-3-butenyl]benzoate

To methyl-4-[2-(4-fluorophenyl)-2-oxoethyl]benzoate (0.48 g, 1.76 mmol) in DMF (5 ml) at 0° C. was added NaH (0.05 g), 2.08 mmol). After a period of 0.5 h, a solution of cinnamyl bromide (0.35 g) in DMF (5 ml) was added to the reaction mixture. The reaction mixture was stirred at r.t. for 1 hour. Ammonium acetate saturated solution (20 ml) was added and the mixture was extracted with ethyl acetate (20 ml). The organic phase was washed with brine and dried over sodium sulfate and evaporated to dryness. The residue was purified by flash chromatography using hexane/ethyl acetate 30% to give 0.43 g of the title compound.

Step 4 4-(bromomethyl)benzaldehyde

To a THF-toluene (2.4 L-0.24 L) solution of α-bromo-p-tolunitrile (266.4 g, 1.36 mol) maintained at an internal temperature bellow 0° C. was added DIBAL in hexane (1.0 M) (1.49 L, 1.49 mol) over a period of 2 h. After a period of 1.5 h, the reaction mixture was transferred via canula to a 3N HCl solution (8 L) at 0° C. To the resulting suspension EtOAc (4 L) and THF (0.8 L) were added. After stirring, the organic phase was separated and evaporated to give a yellow solid. The solid was stirred in 20% EtOAc in hexane (1.3 L) for 3 hours. After filtration and drying the title compound was obtained. (210 g).

Step 5 di(tert-butyl)[4-(bromomethyl)phenyl](hydroxy) methylphosphonate

To a solution of di-t-butylphosphite (125 g, 0.64 mol) in THF (2 L) was added LHMDS (0.607 L, 0.643 mol) at −78° C. The lithium salt was transferred via canula to a −70° C. solution of the aldehyde of Step 4 (122 g, 0.612 mol) in THF (2 L). The resulting reaction mixture was warmed slowly to 0° C. After a period of 1 h at 0° C., aqueous $NH_4OAc$ (1.2 L) and isopropyl acetate (1 L) were added to the reaction mixture. The organic phase was separated, dried over $Na_2SO_4$, filtered and evaporated under reduced pressure. To the resulting solid was added 20% EtOAc in hexane (1 L) and the mixture stirred overnight. After filtration, the title compound was obtained as a white solid (184 g).

Step 6 di(tert-butyl) 4-(bromomethyl)benzoylphosphonate

To the alcohol of Step 5 (184 g, 0.468 mol) in EtOAc (8.4 L) was added $MnO_2$ (407 g, 4.68 mol). After a period of 1 h, the reaction mixture was filtered over celite/silica gel. The solvent was evaporated and 10% EtOAc/hexane (0.50 L) was added. The solid was filtered to provide 137 g of the title compound.

Step 7 di (tert-butyl)[4-(bromomethyl)phenyl](difluoro) methylphosphonate

To a toluene (250 mL) solution of 2-methyl-2-butene (17.8 g, 256 mmol) at 0° C. was added DAST (206 g, 1.28 mol). The ketone of Step 6 (50.0 g, 128 mmol) was then added portionwise. After a period of 18 h at r.t., the reaction mixture was transferred dropwise to a mixture of $NaHCO_3$ saturated (1.2 L), EtOAc (1.2 L), and $Et_3N$ (250 mL) at 0° C. The organic phase was evaporated, dried over $Na_2SO_4$, filtered and evaporated under reduced pressure. The compound was purified over silica gel with 20% EtOAc in hexane to provide 29.5 g of material.

Step 8 methyl 4-[(E)-1-{4-[[di(tert-butoxy)phosphoryl] (difluoro)methyl]benzyl}-1-(4-fluorobenzoyl)-4-phenyl-3-butenyl]benzoate To a solution of methyl 4-[(E)-1-(4-fluorobenzoyl)-4-phenyl-3-butenyl]benzoate (racemate) (0.430 g, 1.10 mmol), 18 crown 6 (0.236 g) and a catalytic amount of tetrabutylammonium iodide in THF (5 ml) degassed at −78° C. was added potassium tert-butoxide 1 M in THF (1.1 ml, 1.10 mmol). After a period of 0.5 h, a solution of di(tert-butyl) [4-(bromomethyl)phenyl](difluoro) methylphosphonate (0.46 g, 1.11 mmol) in THF (5 ml) was added to the reaction mixture, and the reaction mixture was then stirred at room temperature for 1 hour. Saturated ammonium acetate solution (20 ml) was added and the mixture was extracted with ethyl acetate (20 ml). The organic phase was washed with brine and dried over sodium sulfate, filtered and evaporated to dryness. The residue was purified by flash chromatography using hexane/ethyl acetate 15% containing 1% triethylamine giving 0.39 g of the title compound.

$^1$H NMR ($CD_3COCD_3$) δ 1.45(18H, s), 3.05 (2H, m), 3.60 (2H, m), 3.90 (3H, s) 6.25 (2H, m), 6.85 (2H, d), 7.08(2H, t), 7.18–7.40 (9H, m), 7.60 (2H, m),7.95 (2H, d).

Step 9 difluoro(4-{4E)-2-(4-fluorobenzoyl)-2-[4-(methoxycarbonyl)phenyl-5-phenyl-4-pentenyl}phenyl) methylphosphonic acid The ester of Step 8 was dissolved in a 9 to 1 mixture of acetic acid/water (15 ml) at room temperature overnight.

The solution was evaporated to dryness to yield 0.26 g of the title compound (racemate).
$^1$H NMR (CD$_3$COCD$_3$) δ 3.05 (2H, m), 3.55 (2H, m), 3.88 (3H, s), 6.20 (2H, m), 6.85 (2H, d), 7.05 (2H, t), 7.10–7.40 (9H, m), 7.60 (2H, m), 8.00 (2H, d).

Example 1a, 1b

Difluoro(4-{(4E))-2-(4-fluorobenzoyl)-2-[4-(methoxy carbonyl)phenyl]-5-phenyl-4-pentenyl}phenyl)methylphosphonic acid (enantiomers)

Step 1 Methyl4-[(E)-1-{4-[[di(tert-butoxy)phosphoryl](difluoro)methyl]benzyl}-1-(4-fluorobenzoyl)-4-phenyl-3-butenyl]benzoate The compound (racemate) of Example 1 Step 8 was separated on HPLC using a Chiralpak Ad column eluting with hexane/isopropanol 50%+5% ethyl acetate.

RT: 7.14 minute enantiomer a: $^1$H NMR (CD$_3$COCD$_3$) δ 1.45 (18H, s), 3.05 (2H, m), 3.60 (2H, m), 3.90 (3H, s), 6.25 (2H, m), 6.85 (2H, d), 7.08 (2H, t), 7.18–7.40 (9H, m), 7.60 (2H, m), 7.95 (2H, d).

RT: 23.67 minute: enantiomer b: $^1$H NMR (CD$_3$COCD$_3$) δ 1.45 (18H, S), 3.05 (2H, m), 3.60 (2H, m), 3.90 (3H, s), 6.25 (2H, m), 6.85 (2H, d), 7.08 (2H, t), 7.18–7.40 (9H, m), 7.60 (2H, m), 7.95 (2H, d).

Step 2 Difluoro(4-{(4E)-2-(4-fluorobenzoyl)-2-[4-(methoxycarbonyl)phenyl]-5-phenyl-4-pentenyl}phenyl)methylphosphonic acid The enantiomers of Step 1 were treated as described in Example 1 Step 9.

Example 1a $^1$H NMR (CD$_3$COCD$_3$) δ 3.05 (2H, m), 3.55 (2H, m), 3.88 (3H, s), 6.20 (2H, m), 6.85 (2H, d), 7.05 (2H, t), 7.10–7.40 (9H, m), 7.60 (2H, m), 8.00 (2H, d).

Example 1b $^1$H NMR (CD$_3$COCD$_3$) δ 3.05 (2H, m), 3.55 (2H, m), 3.88 (3H, s), 6.20 (2H, m), 6.85 (2H, d), 7.05 (2H, t), 7.10–7.40 (9H, m), 7.60 (2H, m), 8.00 (2H, d).

Example 2

(4-{-2-{4-[difluoro(phosphono)methyl]benzyl}-3-(4-fluorophenyl)-2-[4-(methoxycarbonyl)phenyl]-3-oxopropyl}phenoxy)-2,2-difluoroacetic acid Step 1 methyl 4-[1-{4-[2-(tert-butoxy)-1,1-difluoro-2-oxoethoxy]benzyl}-2-(4-fluorophenyl)-2-oxoethyl]benzoate To a solution of methyl-4-[2-(4-fluorophenyl)-2-oxoethyl]benzoate (0.150 g, 0.551 mmol) (Example 1, Step 2) in degassed THF at −20° C. was added potassium tert-butoxide (0.606 ml), followed by a solution of tert-butyl 2-[4-(bromomethyl)phenoxy]-2,2-difluoroacetate (H. Fretz, *Tetrahedron* 54, 4849, 1998) (0.203 g, 0.604 mmol) in THF (0.5 ml). The reaction was allowed to warm slowly to room temperature, and was then quenched with saturated ammonium acetate solution and extracted with ethyl acetate. The organic phase was dried over sodium sulfate, filtered and evaporated to dryness. The residue was purified by flash chromatography using toluene/ethyl acetate 5% giving 0.176 g of the title compound.

Step 2 methyl 4-[1-{4-[2-(tert-butoxy)-1,1-difluoro-2-oxoethoxy]benzyl}-1-{4-[[di(tert-butoxy)phosphoryl](difluoro)methyl]benzyl}-2-(4-fluorophenyl)-2-oxoethyl]benzoate To a solution of methyl 4-[1-{4-[2-(tert-butoxy)-1,1-difluoro-2-oxoethoxy]benzyl}-2-(4-fluorophenyl)-2-oxoethyl]benzoate (0.176 g, 0.333 mmol)) in degassed THF (1.7 ml), were added at −20° C. 18-crown-6 (0.15 g) and potassium tert-butoxide 1 M in THE (0.379 ml ). Di(tert-butyl) [4-(bromomethyl)phenyl](difluoro)methylphosphonate (0.156 g, 0.378 mmol) was then added and the reaction mixture was allowed to warm to room temperature. The reaction was quenched with saturated ammonium acetate solution and extracted with ethyl acetate. The organic phase was dried over sodium sulfate, filtered and evaporated to dryness. The residue was purified by flash chromatography using hexane/ethyl acetate 20% giving 0.140 g of the title compound.

$^1$H NMR (CD$_3$COCD$_3$) δ 1.42 (27H, 2s), 3.50–3.75 (4H, m), 3.88 (3H, s), 6.90–7.90 (16H, m).

Step 3 (4-{-2-{4-[difluoro(phosphono)methyl]benzyl}-3-(4-fluorophenyl)-2-[4-(methoxycarbonyl)phenyl]-3-oxopropyl}phenoxy)-2,2-difluoroacetic acid The compound of Step 2 was treated with TFA/CH$_2$Cl$_2$ (1/1) at r.t. After a period of 18 h, the solvents were evaporated under reduced pressure to give the title compound (racemate).

$^1$H NMR (CD$_3$COCD$_3$) δ 3.50–3.75 (4H, m), 3.90 (3H, s), 6.90–7.95 (16H, m).

Example 2a, 2b (4-{-2-{4-[difluoro(phosphono)methyl]benzyl}-3-(4-fluorophenyl)-2-{4-(methoxycarbonyl)phenyl]-3-oxopropyl}phenoxy-2,2-difluoroacetic acid (enantiomers)

Step 1 methyl 4-[-1-{4-[2-(tert-butoxy)-1,1-difluoro-2-oxoethoxy]benzyl}-1-{4-[[di(tert-butoxy)phosphory](difluoro)methyl]benzyl}-2-[4-(fluorophenyl)-2-oxoethyl]benzoate The compound (racemate) of Example 2 Step 2 was separated on HPLC using a Chiralpak AD column eluting with hexane/isopropanol (10%–70%). Enantiomer 1 $^1$H NMR (CD$_3$COCD$_3$) δ 1.42 (27H, 2s), 3.50–3.75 (4H, m), 3.88 (3H, s), 6.90–7.90 (16H, m).

Enantiomer 2 $^1$H NMR (CD$_3$COCD$_3$) δ 1.42 (27H, 2s), 3.50–3.75 (4H, m), 3.88 (3H, s), 6.92–7.90 (16H, m).

Step 2 4-{-2-{4-[difluoro(phosphono)methyl]benzyl}-3-(4-fluorophenyl)-2-{4-(methoxycarbonyl)phenyl]-3-oxopropyl}phenoxy-2,2-difluoroacetic acid (enantiomers)

The Enantiomers of Step 1 were treated as described in Example 2 Step 3.

Example 2a $^1$H NMR (CD$_3$COCD$_3$) δ 3.50–3.75 (4H, m), 3.88 (3H, s), 6.90–7.90 (16H, m).

Example 2b $^1$H NMR (CD$_3$COCD$_3$) δ 3.50–3.75 (4H, m), 3.88 (3H, s), 6.90–7.90 (16H, m).

Example 3

4-[2-{4-[difluoro(phosphono)methyl]benzyl}-2-(4-{[2,5-dimethylanilino)carbonyl]amino}phenyl)-1,1-difluoro-3-(4-fluorophenyl)-3-oxopropyl]phenylphosphonic acid Step 1 4-[2-(4-fluorophenyl)-2-oxoethyl]benzoic acid To a solution of methyl 4-[2-(4-fluorophenyl)-2-oxoethyl]benzoate (1.00 g, 3.67 mmol) dissoved in ethanol (18 ml) was added sodium hydroxide 2M (18 ml). The mixture was refluxed for 15 minutes The reaction was cooled and evaporated to removed ethanol. The aqueous residue was acidified with HCl 2 M and extracted with ethyl acetate. The organic fraction was dried over sodium sulfate, filtered and evaporated to give (0.9 g) of the title compound.

Step 2 N-(2,5-dimethylphenyl)-N-{4-[2-(4-fluorophenyl)-2-oxoethyl]phenyl}urea

To a solution of 4-[2-(4-fluorophenyl)-2-oxoethyl] benzoic acid (0.100 g, 0.387 mmol) in acetonitrile was added proton sponge ((0.083 g) and diphenylphosphoryl azide (0.106 g). The reaction mixture was refluxed for 30 minutes. 2,5-dimethyl aniline (0.047 g, 0.388 mmol) was added and the mixture was refluxed another 30 minutes. The reaction was quenched with HCl 1 M and extracted with ethyl acetate, dried over sodium sulfate, filtered and evaporated to dryness. The residue was purified using flash chromatography eluting with hexane/ethyl acetate 40% to give (0.052 g) of the title compound.

Step 3 di(tert-butyl)4-[2-{4-[[di(tert-butoxy)phosphoryl] (difluoro)methyl]benzyl}-2-(4-{[(2,5-dimethylanilino) carbonyl]amino}phenyl)-1,1-difluoro-3-(4-fluorophenyl)-3-oxopropyl]phenylphosphonate To a solution of N-(2,5-dimethylphenyl)-N-{4-[2-(4-fluorophenyl)-2-oxoethyl]phenyl}urea (0.032 g, 0.088 mmol) at −70° C. in DMF (3 ml) was added potassium tert-butoxide (0.19 ml). The reaction mixture was stirred 15 minutes. A solution of di(tert-butyl) [4-(bromomethyl) phenyl](difluoro)methylphosphonate (0.077 g, 0.186 mmol) in DMF (1 ml) was added. The temperature was raised to 0° C., and the reaction was quenched with saturated ammonium chloride solution and extracted with ethyl acetate. The organic phase was dried over sodium sulfate, filtered and evaporated to dryness. The residue was purified using flash chromatography eluting with hexane/ethyl acetate 50% to give (0.032 g) of the title compound.

Step 4 4-[2-{4-[difluoro(phosphono)methyl]benzyl}-2-(4-{[2,5-dimethylanilino)carbonyl]amino}phenyl)-1,1-difluoro-3-(4-fluorophenyl)-3-oxopropyl]phenylphosphonic acid Di(tert-butyl) 4-[2-{4-[[di(tert-butoxy)phosphoryl] (difluoro)methyl]benzyl}-2-(4-{[(2,5-dimethylanilino) carbonyl]amino}phenyl)-1,1-difluoro-3-(4-fluorophenyl)-3-oxopropyl]phenylphosphonate (0.032 g) was dissolved in a 9 to 1 mixture of acetic acid/water (5 ml) at room temperature overnight. The solution was evaporated to dryness to yield 0.008 g of the title compound.

$^1$H NMR (CD$_3$COCD$_3$) δ 2.25 (3H,s), 2.28 (3H,s), 3.52–3.75(4H,q), 6.95(4H, d) 7.02–7.25(7H,m), 7.32 (4H, d), 7.72 (2H,m), 7.87 (2H,d).

Example 4

Difluoro(4-{(E)-2-(4-fluorobenzoyl)-2-[4-(isopropyloxycarbonyl)phenyl]-5-phenyl-4-pentenyl}phenyl)methylphosphonic acid Step 1 isopropyl-4-[2-(4-fluorophenyl)-2-oxoethyl]benzoate To a solution of 4-[2-(4-fluorophenyl)-2-oxoethyl] benzoic acid (Example 3, Step 1) (0.600 g, 2.32 mmol) in toluene(25 ml) was added silver carbonate (1.06 g) and isopropyl iodide (0.70 g).The reaction was refluxed for 2 hour. The reaction mixture was filtered on a pad of silica gel and washed with hexane/ethyl acetate 20%. to give (0.3 g) of the title compound.

Step 2 isopropyl -4-[(E)-1-(4-fluorobenzoyl)-4-phenyl-3-butenyl]benzoate

To a solution of isopropyl-4-[2-(4-fluorophenyl)-2-oxoethyl]benzoate(0.970 g, 3.23 mmol) in DMF (10 ml) at 0° C. was added NaH (0.100 g, 4.16 mmol). After a period of 0.5 h to the reaction mixture was added a solution of cinnamyl bromide (0.630 g, 3.21 mmol) in DMF (10 ml), and the reaction was stirred at room temperature for 1 hour. Saturated ammonium acetate solution (20 ml) was added and the mixture was extracted with ethyl acetate (20 ml). The organic phase was washed with brine and dried over sodium sulfate, filtered and evaporated to dryness. The residue was purified by flash chromatography using a gradient from hexane/ethyl acetate 2% to hexanel ethyl acetate 10% giving 0.39 g of the title compound.

Step 3 isopropyl 4-[(E)-1-{4-[[di(tert-butoxy)phosphoryl] (difluoro)methyl]benzyl}-1-(4-fluorobenzoyl)-4-phenyl-3-butenyl]benzoate To a solution of isopropyl 4-[(E)-1-(4-fluorobenzoyl)-4-phenyl-3-butenyl]benzoate (0.390 g, 0.937 mmol), 18-crown-6 (55 mg) and a catalytic amount of tetrabutylammonium iodide in THF (5 ml) degassed at −78° C. was added potassium tert-butoxide 1 M in THF (0.93 ml). After a period of 0.5 h, to the reaction mixture was added a solution of di(tert-butyl) [4-(bromomethyl)phenyl](difluoro) methylphosphonate(0.390 g, 0.946 mmol) in THF (5 ml). After stirring for 1 h at r.t., saturated ammonium acetate solution (20 ml) was added and the mixture was extracted with ethyl acetate (20 ml). The organic phase was washed with brine, dried over sodium sulfate and evaporated to dryness. The residue was purified by flash chromatography using hexane/ethyl acetate 15% plus 1% triethylamine giving 0.09 g of the title compound.

Step 4 difluoro(4-{(E)-2-(4-fluorobenzoyl)-2-[4-(isopropyloxycarbonyl)phenyl]-5-phenyl-4-pentenyl}phenyl)methylphosphonic acid The product from Step 3 (0.09 g) was dissolved in a 9 to 1 mixture of acetic acid/water (5 ml) at room temperature overnight. The solution was evaporated to dryness to yield 0.04 g of the title compound.

$^1$H NMR (CD$_3$COCD$_3$) δ 1.35(6H,d), 3.05 (2H, m), 3.60 (2H, m) 5.20 (1H, m) 6.22 (2H,m) 6.85 (2H,d), 7.10 (2H, t), 7.12–7.40 (9H,m) 7.62 (2H, m), 8.00 (2H,d).

Example 5

(4-{2-{4-[difluoro(phosphono)methyl]benzyl}-3-(4-fluorophenyl)-2-[4-(isopropoxycarbonyl)phenyl]-3-oxopropyl}phenyl(difluoro)methylphosphonic acid Step 1 Isopropyl 4-[1,1-bis{4-[[di(tert-butoxy)phosphoryl] (difluoro)methyl]benzyl}-2-(4-fluorophenyl)-2-oxoethyl] benzoate To a solution of isopropyl-4-[2-(4-fluorophenyl)-2-oxoethyl]benzoate (Example 4, Step 1) (0.100 g, 0.333 mmol), 18-crown-6 (20 mg) and a catalytic amount of tetrabutylammonium iodide in THF (3 ml) degassed at −78° C. was added potassium tert-butoxide 1 M in THF (0.66 ml, 0.66 mmol). After a period of 0.5 h, to the reaction mixture was added a solution of di(tert-butyl) [4-(bromomethyl) phenyl]-(difluoro)methylphosphonate (0.270 g, 0.655 mmol) in THF (5 ml). The reaction was stirred at r.t. for 1 hour, and then saturated ammonium acetate solution (20 ml) was added and the mixture was extracted with ethyl acetate (20 ml). The organic phase was washed with brine and dried over sodium sulfate and evaporated to dryness. The residue was purified by flash chromatography using hexane/ethyl acetate 15% plus 1% triethylamine giving 0.09 g of the title compound.

Step 2 (4-{2-{4-[difluoro(phosphono)methyl]benzyl}-3-(4-fluorophenyl)-2-[4-(isopropoxycarbonyl)phenyl]-3-oxopropyl}phenyl(difluoro)methylphosphonic acid The product from Step 1 (0.09 g) was dissolved in a 9 to 1 mixture of acetic acid/water (5 ml) at room temperature overnight. The solution was evaporated to dryness to yield 0.07 g of the title compound.

$^1$H NMR (CD$_3$OD) δ 1.35 (6H, d), 3.55 (4H, q), 5.22 (1H,m) 6.80 (4H,d), 6.98 (2H, t), 7.23 (2H,d) 7.50 (4H,d), 7.60 (2H,m) 7.95(2H, d).

Example 6

(4-{4-{4-[difluoro(phosphono)methyl]benzyl}5-(4-fluorophenyl)-4-[4-isopropoxycarbonyl)phenyl-5-oxopentyl}phenyl)(difluoro)methylphosphonic acid Step 1 diethyl difluoro{4-[(E)-3-hydroxy-1-propenyl]phenyl}methylphosphonate To a solution of diethyl difluoro(4-iodophenyl)methylphosphonate T. R. Burke *Tetrahedron Letters,* 551, 1994, (2.50 g, 6.91 mmol) in DMF (25 ml) was added allyl alcohol (1.3 ml), silver acetate (1.1 g), palladium acetate (0.075 g), and triphenyl phosphine (0.175 g). The reaction mixture was refluxed for 2 hours. After cooling to room temperature the reaction was diluted with water and extracted with ethyl acetate. The mixture was filtered through a pad of celite. The organic layer was separated and washed with water, dried over magnesium sulfate, filtered and evaporated. The residue was purified using flash chromatography with hexane/ethyl acetate 75% to give 0.6 g of the title compound.

Step 2 diethyl{4-[(E)-3-bromo-1-propenyl]phenyl}(difluoro) methylphosphonate

To a solution of diethyl difluoro{4-[(E)-3-hydroxy-1-propenyl]phenyl}methylphosphonate (0.600 g, 1.86 mmol) and triphenylphosphine (0.650 g, 2.48 mmol)in THF (10 ml) at 0° C. was added NBS (0.430 g, 2.42 mmol) in one portion. The reaction was stirred for 1 hour at 0° C. The solvent was evaporated to dryness, and the residue was purified using flash chromatography with hexane/ethyl acetate 33% to give 0.7 g of the title compound.

$^1$H NMR (CD$_3$COCD$_3$) δ 1.28(6H,t), 4.15(4H,m), 4.28 (2H, d), 6.65(1H,m), 6.85(1H,d), 7.62(4H,m).

Step 3 isopropyl 4-[1-{4-[[di(tert-butoxy)phosphoryl](difluoro)methyl]benzyl}-2-(4-fluorophenyl)-2-oxoethyl]benzoate To a solution of isopropyl-4-[2-(4-fluorophenyl)-2-oxoethyl]benzoate (0.130 g, 0.433 mmol), (Example 4, Step 1) 18-crown-6 (0.03 g) in THF (2.2 ml ) at −2020 C. was added a solution of potassium tert-butoxide 1 M in THF (0.475 ml). To the reaction mixture was added a solution of di(tert-butyl) [4-(bromomethyl)phenyl](difluoro) methylphosphonate (0.196 g, 0.475 mmol) in THF (5 ml). The reaction was stirred at room temperature for 1 hour, and then saturated ammonium acetate solution (20 ml) was added and the mixture was extracted with ethyl acetate (20 ml). The organic phase was washed with brine, dried over sodium sulfate, filtered, and evaporated to dryness. The residue was purified by flash chromatography using hexane/ethyl acetate 15% plus 1% triethylamine giving 0.05 g of the title compound.

Step 4 isopropyl 4-[(E)-1-{4-[[di(tert-butoxy)phosphoryl](difluoro)methyl]benzyl}-4-{4-[(diethoxyphosphoryl)(difluoro)methyl]phenyl}-1-(4-fluorobenzoyl)-3-butenyl]benzoate To a solution of isopropyl 4-[1-{4-[[di(tert-butoxy)phosphoryl](difluoro)methyl]benzyl}-2-(4-fluorophenyl)-2-oxoethyl]benzoate (0.050 g, 0.079 mmol), 18-crown-6 (0.01 g), and a catalytic amount of tetrabutylammonium iodide in THF (2 mL) at −20° C. was added a solution of potassium tert-butoxide 1 M in THF (0.09 ml). A solution of diethyl{4-[(E)-3-bromo-1-propenyl]phenyl}(difluoro) methylphosphonate (0.033 g, 0.166 mol) in THF (0.05 ml) was then added, and the reaction was stirred at r.t. for 1 hour. Saturated ammonium acetate solution (20 ml) was added and the mixture was extracted with ethyl acetate (20 ml). The organic phase was washed with brine, dried over sodium sulfate, filtered, and evaporated to dryness. The residue was purified by flash chromatography using hexane/ethyl acetate 40% plus 1% triethylamine giving 0.02 g of the title compound.

Step 5 isopropyl 4-[1-{4-[[di(tert-butoxy)phosphoryl](difluro)methyl]benzyl}-4-{4-[(diethoxyphosphoryl)(difluoro)methyl]phenyl}-1-(4-fluorobenzoyl)butyl]benzoate To a solution of isopropyl 4-[(E)-1-{4-[[di(tert-butoxy)phosphoryl](difluro)methyl]benzyl}-4-{4-[(diethoxyphosphoryl)(difluoro)methyl]phenyl}-1-(4-fluorobenzoyl)-3-butenyl]benzoate in ethyl acetate was added palladium on charcoal. The mixture ws then hydrogenated on a Parr apparatus at 50 psi. The reaction mixture was filtered and evaporated to give 0.02 g of the title compound.

Step 6 (4-{4-{4-[difluoro(phosphono)methyl]benzyl}5-(4-fluorophenyl)-4-[4-isopropoxycarbonyl)phenyl]-5-oxopentyl}phenyl)(difluoro)methylphosphonic acid To a solution of isopropyl 4-[1-{4-[[di(tert-butoxy)phosphoryl](difluro)methyl]benzyl}-4-{4-[(diethoxyphosphoryl)(difluoro)methyl]phenyl}-1-(4-fluorobenzoyl)butyl]benzoate (0.02 g) in chloroform (0.20 ml) was added TMSBr (0.05 ml). The reaction mixture was stirred at room temperature overnight. After evaporation to dryness, the residue was quenched with methanol (0.02 ml) and evaporated to give 0.010 g of the title compound.

$^1$H NMR (CD$_3$COCD$_3$) 1.40 6H, m), 1.50–3.50 (8H, m), 5.20 (1H, m), 6.40–8.00 (16H, m).

Example 7

{4-[2-{4-[(diethylamino)carbonyl]phenyl}-2-{4-[difluorophosphono)methyl]benzyl3(4-fluorophenyl)-3-oxopropyl]phenyl}(difluoro)methylphosphonic acid Step 1 N,N,-diethyl-4-[2-(4-fluorophenyl)-2-oxoethyl]benzamide To a solution of 4-[2-(4-fluorophenyl)-2-oxoethyl]benzoic acid (0.560 g, 2.17 mmol, Example 3, Step 1), triethylamine (0.620 ml), and diethylamine (0.230 ml) in dichloromethane (5 ml) at room temperature was added bis(2-oxo-3-oxazolidinyl)-phosphinic chloride (0.560 g). After 3 hours, HCl 1M (10 ml) was added and the product was extracted with dichloromethane (10 ml). The organic phase was washed with brine, dried over sodium sulfate, filtered and evaporated to dryness. The residue was purified by flash chromatography using hexane/ethyl acetate 50% giving 0.44 g of the title compound.

Step 2 di(tert-butyl){4-[2-{4[[di(tert-butoxy)phosphoryl](difluoro)methyl]benzyl}-2-{4-[(diethylamino)carbonyl]phenyl}-3-(4-fluorophenyl)-3-oxopropyl]phenyl}(difluoro) methylphosphonate To a solution of N,N-diethyl-4-[2-(4-fluorophenyl)-2-oxoethyl]benzamide (0.44 g, 1.41 mmol), 18 crown 6 and a catalytic amount of tetrabutylammonium iodide in THF (10 ml) degassed at −78° C. was added a solution of potassium tert-butoxide 1 M in THF (3.1 ml). After a period of 0.5 h, to the reaction mixture was added a solution of di(tert-butyl) [4-(bromomethyl)phenyl](difluoro) methylphosphonate (1.32 g, 3.20 mmol) in THF (10 ml). The reaction was stirred at r.t. overnight, at which point saturated ammonium acetate solution (20 ml) was added and the mixture was extracted with ethyl acetate (20 ml). The organic phase was washed with brine, dried over sodium sulfate, filtered, and evaporated to dryness. The residue was purified by flash chromatography using hexane/ethyl acetate 70% plus 1% triethylamine giving 0.2 g of the title compound.

Step 3 {4-[2-{4-[(diethylamino)carbonyl]phenyl}-2-{4-[difluoro phosphono)methyl]benzyl}-3-(4-fluorophenyl)-3-oxopropyl]phenyl}(difluoro)methylphosphonic acid The product from Step 3 (0.200 g, 0.204 mmol) was dissolved in a 9 to 1 mixture of acetic acid/water (15 ml) at room temperature overnight. The solution was evaporated to dryness to yield 0.12 g of the title compound.

$^1$H NMR (CD$_3$COCD$_3$) δ 1.15 (4H,m), 3.22 (2H, m), 3.45 (2H,m) 3.55(2H, d) 3.70(2H, d), 6.98(4H,d), 7.15 (2H,t), 7.22 (2H,m),7.30 (2H,d), 7.37 (4H,d), 7.75(2H,m).

Example 8

Difluoro(4-{(E)-2-(4-fluorobenzoyl)-2-[3-(methoxycarbonyl)phenyl]-5-phenyl-4-pentenyl}phenyl)methylphosphonic acid Step 1 methyl 3-[2-(4-fluorophenyl)-2-oxoethyl]benzoate To a solution of the TMS cyanohydrin from Example 1, Step 1 (3.70 g, 16.6 mmol) in THF (40 mL) under N$_2$ at −78° C. was added slowly a solution of LHMDS (18.2 mL, 18.2 mmol, 1.0 M/THF). After 15 min. at −78° C., a solution of methyl 3-(bromomethyl)benzoate (3.99 g, 17.4 mmol) in THF (20 mL) was added via double-tipped needle. The reaction was allowed to warm slowly to r.t. over 1 h. and was then stirred at r.t. for 2.5 h. Bu$_4$NF (33 mL, 33 mmol, 1M/THF) was then added and the mixture was stirred for 1 h. Saturated NH$_4$Cl (20 mL) was then added and the product was extracted with EtOAc. The organic phase was washed with H$_2$O and brine, and was then dried (MgSO$_4$), filtered, and evaporated. The residue was stirred vigourously with 1:5 Et$_2$O:hexane (50 mL) for 1 h, and the product was then obtained by filtration. This material was dissolved in CH$_2$Cl$_2$ and filtered through a plug of silica gel, washing with CH$_2$Cl$_2$. After removal of solvent, a pale yellow solid (3.4 g) was obtained.

$^1$H NMR (CD$_3$COCD$_3$), 3.85 (3H, s), 4.50 (2H, s), 7.23–7.33 (2H, m), 7.42–7.50 (1H, m), 7.54–7.61 (1H, m), 7.85–7.93 (1H, m), 7.93–7.97 (1H, m), 8.14–8.23 (2H, m).

Step 2: Methyl 3-[(E)-1-(4-fluorobenzoyl)-4-phenyl-3-butenyl]benzoate

To a solution of the product from Step 1 (1.0 g, 3.7 mmol) and cinnamyl bromide (0.72 g, 3.7 mmol) in DMF (15 mL) at 0° C. under N$_2$ was added the NaH (121 mg, 4.0 mmol, 80% in oil). After 20 min. at 0° C., the reaction was stirred for 1 h at r.t. Saturated NH$_4$Cl (15 mL) was then added and the product was extracted with Et$_2$O. The organic phase was washed with H$_2$O and brine, and was then dried (MgSO$_4$) filtered, and evaporated. The residue was purified by flash chromatography (1:10 EtOAc:hexane) to give a colourless oil (1.26 g).

$^1$H NMR (CD$_3$COCD$_3$) δ 2.66–2.7–7 (1H, m), 3.04–3.12 (1H, m), 3.84 (3H, s), 5.08–5.15 (1H, m), 6.18–6.27 (1H, m), 6.38–6.47 (1H, m), 7.11–7.29 (7H, m), 7.42–7.49 (1H, m), 7.65–7.71 (1H, m), 7.82–7.88 (1H, m), 8.01–8.05 (1H, m), 8.11–8.19 (2H, m).

Step 3 Methyl 3-[(E)-1-{4-[[di(tert-butoxy)phosphoryl](difluoro)methyl]benzyl}-1-(4-fluorobenzoyl)-4-phenyl-3-butenyl]benzoate To a degassed solution of the product from Step 2 (0.30 g, 0.77 mmol), 18-Crown-6 (102 mg, 0.39 mmol), and Bu$_4$NI (28 mg, 0.077 mmol) in THF at −78° C. was added the KOtBu solution. After 15 min. at −78° C., a solution of di(tert-butyl)(4-(bromomethyl)phenyl)(difluoro)methyl phosphonate (Example 1, Step 7) (319 mg, 0.77 mmol) in THF (3 mL) via double-tipped needle. The cold bath was removed and the reaction was stirred at r.t. for 1.5 h. Saturated NH$_4$Cl solution was then added and the product was extracted with EtOAc. The organic layer was washed with H$_2$O and brine, and was then dried (MgSO$_4$), filtered, and evaporated. The residue was purified by flash chromatography (1:20 Et$_2$O: toluene, 1% Et$_3$N) to give an oil (98 mg).

$^1$H NMR (CD$_3$COCD$_3$) δ 1.41–1.46 (18 H, m), 2.97–3.16 (2H, m), 3.52–3.67 (2H, m), 3.84 (3H, s), 6.16–6.30 (2H, m), 6.81–6.85 (2H, m), 7.04–7.11 (2H, m), 7.16–7.33 (7H, m), 7.42–7.48 (1H, m), 7.50–7.57 (1H, m), 7.57–7.64 (2H, m), 7.87 (1H, s), 7.97–8.02 (1H, m).

Step 4 Difluoro(4-{(E)-2-(4-fluorobenzoyl)-2-[3-(methoxycarbonyl)phenyl]-5-phenyl-4-pentenyl}phenyl)methylphosphonic acid The phosphonate ester from Step 3 (22 mg, 0.03 mmol) was stirred overnight in a solution of HOAc (2 mL) and H$_2$O (0.2 mL). The solvent was removed under vacuum and the residue was co-evaporated 3× with toluene and 2× with acetone to give a pale yellow syrup (20 mg).

$^1$H NMR (CD$_3$COCD$_3$) δ 3.00–3.14 (2H, m), 3.48–3.64 (2H, m), 3.83 (3H, s), 6.13–6.23 (2H, m), 6.78–6.85 (2H, m), 7.03–7.12 (2H, m), 7.12–7.39 (7H, m), 7.39–7.48 (1H, m), 7.48–7.57 (1H, m), 7.57–7.66 (2H, m), 7.78–7.84 (1H, m), 7.94–8.00 (1H, m).

Example 9

{4-[(E)-2-benzoyl-2,5-diphenyl-4-pentenyl]phenyl}(difluoro)methylphosphonic acid Step 1 (E)-1,2,5-triphenyl-4-penten-1-one To a solution of 2-deoxybenzoin (10.0 g, 51 mmol) in DMF (100 mL) was added NaH (1.47 g, 49 mmol, 80% in oil). After 1 h at 0° C., a solution of cinnamyl bromide (10.0 g, 51 mmol) in DMF (20 mL) was added. After a further 2 h at 0° C., the reaction was quenched by the addition of saturated NH$_4$OAc solution, and the product was extracted with EtOAc. The organic layer was washed with H$_2$O and brine, and was then dried (Na$_2$SO$_4$), filtered, and evaporated. The residue was purified by flash chromatography (5% EtOAc:hexane) to give an off-white solid (9.7 g).

$^1$H NMR (acetone, d$_6$) δ 2.64–2.73 (1H, m), 3.03–3.11 (1H, m), 4.95–5.01 (1H, m), 6.18–6.28 (1H, m), 6.41–6.48 (1H, m,), 7.12–7.34 (8H, m), 7.38–7.47 (4H, m), 7.50–7.56 (1H, m), 8.04–8.09 (2H, m).

Step 2 di(tert-butyl){4-[(E)-2-benzoyl-2,5-diphenyl-4-pentenyl]phenyl}(difluoro)methylphosphonate To a degassed solution of the product from Step 1 (5.0 g, 16 mmol), 18-Crown-6 (2.11 g, 8 mmol), and Bu$_4$NI (0.59 g, 1.6 mmol) in THF (150 mL) at −78° C. was added the KOtBu (19.2 mL, 19.2 mmol, 1M THF). After 15 min. a solution of di(tert-butyl){4-(bromomethyl)phenyl](difluoro)methylphosphonate (Example 1, Step 7)(7.93 g, 19.2 mmol) in THF (50 mL) was added slowly via double-tipped needle. The cold bath was then removed and the mixture was stirred for 1 h 20 min. Saturated NH$_4$Cl solution was added, and the product was extracted with EtOAc. The organic layer was washed with H$_2$O and brine, and was then dried (MgSO$_4$), filtered and evaporated. The crude solid was stirred vigourously with 1:5 EtOAc:hexane (100 mL) for 2 h, to give, after filtration, a white solid (racemate) (7.17 g).

$^1$H NMR (CD$_3$COCD$_3$) δ 1.43 (18H, 2s), 2.91–3.10 (2H, m), 3.46–3.58 (2H, m), 6.12–6.26 (2H, m), 6.78–6.83 (2H, m), 7.17–7.33 (11H, m), 7.34–7.44 (3H, m), 7.44–7.54 (3H, m).

Step 3 {4-[(E)-2-benzoyl-2,5-diphenyl-4-pentenyl]phenyl}(difluoro)methylphosphonic acid (racemate)

In the same manner as Example 8, Step 4, was prepared the title compound.

$^1$H NMR (CD$_3$COCD$_3$) δ 2.90–3.08 (2H, m), 3.45–3.58 (2H, m), 6.11–6.18 (2H, m), 6.75–6.82 (2H, m), 7.13–7.42 (14H, m), 7.42–7.55 (3H, m).

Example 9a, 9b

{4-[(E)-2-benzoyl-2,5-diphenyl-4-pentenyl]phenyl}(difluoro)methylphosphonic acid Step 1 di(tert-butyl){4-[(E)-2-Benzoyl-2,5-diphenyl-4-pentenyl]phenyl}(difluoro)methylphosphonate The enantiomers of Example 9 Step 2 were separated on HPLC using a Chiralpak AD column, eluting with 10% isopropanol in hexane.

Enantiomer 1 $^1$H NMR (CD$_3$COCD$_3$) δ 1.43 (9H, 2s), 2.91–3.10 (2H, m), 3.46–3.58 (2H, m), 6.12–6.26 (2H, m), 6.78–6.83 (2H, m), 7.17–7.33 (11H, m), 7.34–7.44 (3H, m), 7.44–7.54 (3H, m).

Enantiomer 2 $^1$H NMR (CD$_3$COCD$_3$) δ 1.43 (9H, 2s), 2.91–3.10 (2H, m), 3.46–3.58 (2H, m), 6.12–6.26 (2H, m), 6.78–6.83 (2H, m), 7.17–7.33 (11H, m), 7.34–7.44 (3H, m), 7.44–7.54 (3H, m).

Step 2 {4-[(E)-2-benzoyl-2,5-diphenyl-4-pentenyl]phenyl}(difluoro)methylphosphonic acid The enantiomers of Step 1 were treated as described for Example 9, Step 3.

Enantiomer 1 $^1$H NMR (CD$_3$COCD$_3$) δ 2.90–3.08 (2H, m), 3.45–3.58 (2H, m), 6.11–6.18 (2H, m), 6.75–6.82 (2H, m), 7.13–7.42 (14H, m), 7.42–7.55 (3H, m).

Enantiomer 2 $^1$H NMR (CD$_3$COCD$_3$) δ 2.90–3.08 (2H, m), 3.45–3.58 (2H, m), 6.11–6.18 (2H, m), 6.75–6.82 (2H, m), 7.13–7.42 (14H, m), 7.42–7.55 (3H, m).

Example 10

(4-{2-{4-[difluoro(phosphono)methyl]benzyl}-3-(4-fluorophenyl)-2-[4-(methoxycarbonyl)phenyl]-3-oxopropyl}phenyl)(difluoro)methylphosphonic acid The title compound was prepared as described for Example 5.

$^1$H NMR (CD$_3$COCD$_3$) δ 3.60 (4H, m), 3.90 (3H, s), 6.90–8.00 (16H, m).

Example 11

(4-{(4E)-2-(3,4-dichlorobenzoyl)-2-[4-(methoxycarbonyl)phenyl]-5-phenyl-4-pentenyl}phenyl)(difluoro)methylphosphonic acid The title compound was prepared as described in Example 1.

$^1$H NMR (CD$_3$COCD$_3$) δ 3.00 (2H, m), 3.55 (2H, m), 3.90 (3H, s), 6.20–8.00 (18H, m),

Example 12

(4-{2-Benzyl-2-(4-fluorophenyl)-3-[4-(methoxycarbonyl)phenyl]-3-oxopropyl}phenyl)(difluoro)methylphosphonic acid The title compound was prepared as described in Example 1.

$^1$H NMR (CD$_3$COCD$_3$) δ 3.50–3.70 (4H, m), 3.90 (3H, s), 6.85–7.95 (17H, m).

Example 13

Difluoro(4-{2-(4-fluorophenyl)-2-[4-(methoxycarbonyl)benzyl]-3-[4-(methoxycarbonyl)phenyl]-3-oxopropyl}phenyl)methylphosphonic acid The title compound was prepared as described in Example 1.

$^1$H NMR (CD$_3$COCD$_3$) δ 3.62–3.70 (4H, m), 3.80 (3H, s), 3.90 (3H, s).

Example 14

Difluoro(4-{2-[4-(methoxycarbonyl)benzyl]-3-oxo-2,3-diphenylpropyl}phenyl)methylphosphonic acid The title compound was prepared as described in Example 1.

$^1$H NMR (CD$_3$COCD$_3$) δ 3.50–3.65 (4H, m), 3.80 (3H, s), 6.90–7.70 (18H, m).

Example 15

4-[1,1-Bis{4-[difluoro(phosphono)methyl]benzyl}-2-(4-fluorophenyl)-2-oxoethyl]benzoic acid The compound of Example 10 (0.080 g, 0.112 mmol) was treated with NaOH in THF/MeOH at 60° C. After a period of 18 h, Dowex H$^+$ was added. After a few minutes, the resin was filtered and the solvent evaporated to provide the title compound.

$^1$H NMR (CD$_3$COCD$_3$) δ 3.50 (4H, s), 6.90–8.00 (16 H, m).

Example 16a, 16b

4-[1-{4-[carboxy(difluoro)methoxy]benzyl}-1-{4-[difluoro(phosphono)methyl]benzyl}-2-(4-fluorophenyl-2-oxoethyl]benzoic acid Step 1 tert-butyl 4-[2-(4-fluorophenyl)-2-oxoethyl]benzoate p-Bromomethyl benzoic acid (8.1 g) was refluxed with α,α dichloromethyl methyl ether (50 mL) for 1 h. The reaction mixture was evaporated to dryness, co-distilled with toluene twice and pumped under high vacuum. To the acid chloride redissolved in THF (100 mL) at −78° C. was added potassium tert-butoxide 1M in THF (30 mL) dropwise. Then temperature was raised to −20° C. and stirred for 1 h. The reaction mixture was quenched with NH$_4$OAc and extracted with EtOAc. The organic phase was dried over Na$_2$SO$_4$ and evaporated to yield 50 g of tert-butyl-4-(bromomethyl)benzoate.

To a solution of 2-(4-fluorophenyl)-2-[(trimethylsilyl)oxy]acetonitrile (0.8 g) (Example 1, Step 1) in degassed THF (15 mL) at −78° C. was added LHMDS 1 M in THF (3.6 mL). After a period of 15 minutes, a solution or tert-butyl-4-(bromomethyl) benzoate (1.0 g) in THF (2 mL) was added at −78° C. After 1 h at room temperature, tetrabutylammonium fluoride solution 1 M in THF (3.69 mL) was added. The reaction was stirred for 10 minutes, at which point water was added and the mixture was extracted with ethyl acetate. The organic phase was dried over sodium sulfate and evaporated to dryness. The residue was purified by flash chromatography using hexane/ethyl acetate 30% giving 0.56 g of the title compound.

$^1$H NMR (CD$_3$COCD$_3$) δ 1.58 (9H, s, 4.50 (2H, s), 7.28 (2H, t), 7.42 (2H, d), 7.92 (2H, d), 8.15 (2H, q),

Step 2 tert-butyl 4-[1-{4-[2-(tert-butoxy)-1,1-difluoro-2-oxoethoxy]benzyl}-2-(4-fluorophenyl)-2-oxoethyl]benzoate The title compound was prepared as described in Example 2 Step 1.

Step 3 tert-butyl 4-[1-{4-[2-(tert-butoxy)-1,1-difluoro-2-oxoethoxy]benzyl}-1-{4-[[di(tert-butoxy)phosphoryl](difluoro)methyl]benzyl}-2-(4-fluorophenyl)-2-oxoethyl]benzoate The title compound was prepared as described in Example 2, Step 2. The two enantiomers were separated on HPLC using a ChiralpakAD column.

Enantiomer a $^1$H NMR (CD$_3$COCD$_3$) δ 1.40 (18H, s), 1.45 (9H, s), 1.50 (9H, s), 3.55–3.75 (4H, m), 6.90–7.90 (16H, m).

Enantiomer b $^1$H NMR (CD$_3$COCD$_3$) δ 1.40 (18H, s), 1.45 (9H, s), 1.50 (9H, s), 3.55–3.75 (4H, m), 6.90–7.90 (16H, m).

Step 4 4-[1-{4-[carboxy(difluoro)methoxy]benzyl}-1-{4-[difluoro(phosphono)methyl]benzyl}-2-(4-fluorophenyl)-2-oxoethyl]benzoic acid Each enantiomer of Step 3 was treated with TFA/H$_2$O (9/1) for 5 h.

Enantiomer 16a $^1$H NMR (CD$_3$COCD$_3$) δ 3.50–3.70 (4H, m), 6.90–8.00 (16H, m).

Enantiomer 16b $^1$H NMR (CD$_3$COCD$_3$) δ$^1$H NMR (CD$_3$COCD$_3$) δ 3.50–3.70 (4H, m), 6.90–8.00 (16H, m).

Example 17

{4-[2-[4-(Tert-butoxycarbonyl)phenyl]-2-{4-[difluoro(phosphono)methyl)benzyl}-3-(4-fluorophenyl)-3oxopropyl]phenyl}(difluoro)methylphosphonic acid The title compound was prepared as described in Example 5 using the ketone of Example 16 Step 1.

$^1$H NMR (CD$_3$COCD$_3$) δ 1.60 (9H, s), 3.60 (4H, m), 6.90–8.05 (16H, m).

Example 18

(2-bromo-4-{(E)-2-(4-fluorobenzoyl)-2-[4-(methoxycarbonyl)phenyl]-5-phenyl-4-pentenyl}phenyl)(difluoro)methylphosphonic acid Step 1 2-bromo-4-(bromomethyl)benzoic acid 2-Bromo-4-methylbenzoic acid (33.5 g, 156 mmol, 1 eq) and N-Bromosuccinimide (40.7 g, 233 mmol, 1.5 eq) were dissolved in refluxing 1,2-dichloroethane (600 ml) and a catalytic amount of AIBN was added. The mixture was left stirring under a lamp and under nitrogen for 1 hour. The solvent was removed and the mixture was partitioned between 600 ml of water and 600 ml EtOAc. The organic layer was washed twice with water (600 ml), washed once with brine (600 ml) and then dried with sodium sulfate. The solvent was removed and the crude mixture was triturated with 10% EtOAc/Hexane for 2 hours to give 23.8 g (52%) of the title compound.

Step 2 [2-bromo-4-(bromomethyl)phenyl]methanol

The compound of Step 1 (23.8 g, 81 mmol, 1 eq) was dissolved in THF under nitrogen at 0° C. A 1M borane solution in THF (242 ml, 242 mmol, 3 eq) was then added dropwise and the mixture was stirred at RT for 1 hour under nitrogen. The solution was cooled in an ice bath and 125 ml of methanol was then added slowly. The solvent was removed and the mixture partitioned between 400 ml of water and 400 ml of 20% THF/EtOAc. The aqueous layer was washed 3 times with 400 ml of 20% THF/EtOAc and the combined organic layers were dried with sodium sulfate. The solvent was removed and 19.7 g (87%) of the title compound was obtained.

Step 3 4-(bromomethyl)-2-bromobenzaldehyde

The compound of Step 2 (8 g, 29 mmol, 1 eq) was dissolved in 10% EtOH/EtOAc (300 ml) and 5 eq of MnO$_2$ (12.4 g, 142 mmol) was added every hour for 6 hours. The mixture was filtered through Celite and solvent was removed. 6.5 g (80%) of the title compound was obtained.

Step 4 di(tert-butyl)[2-bromo-4(bromomethyl)phenyl](hydroxy)methylphosphonate

Di-tert-butyl phosphite (14.8 g, 76.3 mmol, 1.05 eq) was dissolved in 200 ml THF at −78° C. under nitrogen and 72 ml (1.05 eq) of 1.06M Lithium bis(trimethylsilyl)amide in THF was added over 30 min. The mixture was left stirring at −78° C. under nitrogen for 30 min and then added to a solution of the compound of Step 3 (20.2 g, 72.7 mmol, 1 eq) in 200 ml THF at −78° C. The solution was warmed to 0° C. and then poured into 400 ml of half saturated aqueous ammonium acetate. The layers were separated and the aqueous layer was washed with 400 ml isopropyl acetate. The organic layers were combined, dried with sodium sulfate and the solvent. removed. The crude solid was then triturated with 15% EtOAc/hexane for 2 hours and 30.4 g (89%) of the title compound was obtained.

Step 5 di(tert-butyl)2-bromo-4-(bromomethyl)benzoylphosphonate

The compound of Step 4 was dissolved in acetone, and MnO$_2$ (40 equiv.) was added. The mixture was stirred vigorously for 2–7 hours, then filtered through Celite. The solvent was removed to provide the title compound. Alternatively, the title compound can be prepared by Swern oxidation of the compound of Step 4.

Step 6 di(tert-butyl)[2-bromo-4-(bromomethyl)phenyl](difluoro)methylphosphonate

To di(tert-butyl)-2-bromo-4-(bromomethyl)benzoylphosphonate (8.0 g, 17 mmol) was added 2-methyl-2-butene (8.0 mL). To the previous mixture at 0° C. was added diethylamino sulfur trifluoride (40 mL). After a period of 24 h, the reaction mixture was poured into 2.2L of 1/1 ethylacetate-hexane, diisopropylethylamine (90 mL) and saturated NaHCO$_3$ (400 mL) at 0° C. The organic phase was separated, dried over Na$_2$SO$_4$, filtered and evaporated. The crude material was purified by flash chromatography (20% ethyl acetate in hexane) over silica gel previously washed with 20% ethyl acetate hexane containing 1% of Et$_3$N to give 5.0 g of the title compound.

$^1$H NMR (400 MHz, CDCl$_3$) δ 1.50 (18H, s), 4.40 (2H, s), 7.40 (1H, d), 7.60 (1H, d), 7.65 (1H, d).

Step 7 (2-bromo-4-{(E)-2-(4-fluorobenzoyl)-2-[4-(methoxycarbonyl)phenyl]-5-phenyl-4-pentenyl}phenyl)(difluoro)methylphosphonic acid The title compound was then prepared as described for Example 1 Steps 3, 8 (using di(tert-butyl)[2-bromo-4(bromethyl)phenyl](difluoro) methylphosponate) and 9. MS m/z=687.

Example 19

{2-bromo-4-[3-(phenyl)-2-methyl-3-oxo-2-phenylpropyl]phenyl}(difluoro)methylphosphonic acid Step 1 1,2-diphenyl-1-propanone To deoxybenzoin (0.500 g, 2.55 mmol) in THF (12 mL) at −78° C. were added a THF solution of potassium tert-butoxide 1M (2.5 mL, 2.55 mmol) and MeI (0.396 mL). After a period of 0.5 h, at room temperature, NH$_4$OAc aqueous was added to the reaction mixture. The organic phase was separated, dried over NaSO$_4$, filtered and evaporated. The residue was purified by flash chromatography to give the title compound.

Step 2 {2-bromo-4-[3-(phenyl)-2-methyl-3-oxo-2-phenylpropyl]phenyl(difluoro)methylphosphonic acid The title compound was prepared as described in Example 1 Steps 8 and 9 using the alkylating agent of Example 18 Step 6.

$^1$H NMR (CD$_3$COCD$_3$) δ 1.55 (3H, s), 3.40 (2H, s), 6.80–7.50 (13H, m).

Example 20

{4-[(E)-2-Benzoyl-2,5-diphenyl-4-pentenyl]-2-bromophenyl}(difluoro)methylphosphonic acid The title compound was prepared from 2-deoxybenzoin using the method described in Example 1 Step 3 followed by Steps 8 (alkylating agent of Example 18 Step 6) and 9.

$^1$H NMR (CD$_3$COCD$_3$) δ 3.02 (2H, m), 3.50 (2H, m), 6.10–7.80 (20H, m).

Example 21

[2-Bromo-4-(2-}4-[difluoro(phosphono)methyl]benzyl}-3-oxo-2,3-diphenylpropyl)phenyl](difluoro)methylphosphonic acid Step 1  di(tert-butyl)difluoro(4-(3-oxo-2,3-diphenylpropyl)phenyl]methylphosphonate To a solution of 2-deoxybenzoin (10 g, 51 mmol) and di(t-butyl)[4-(bromomethyl)phenyl](difluoro)methylphosphonate (Example 1 Step 7, 11.5 g, 28 mmol) in dry DMF (150 mL) at 0° C. was added 80% NaH (0.9 g, 30 mmol). The ice bath was removed and the mixture was stirred for 1 h at r.t. The reaction was quenched by the addition of saturated NH$_4$Cl solution. The product was extracted with Et$_2$O and the organic phase was washed with H$_2$O and brine. After drying (MgSO$_4$), filtration, and removal of solvent, the crude product was stirred for 1 hour in 1:10 EtOAc:hexane to give a white solid (8.8 g).

Step 2  di(tert-butyl)[2-bromo-4-(2-{4-[[di(tert-butoxy)phosphoryl](difluoro)methyl]benzyl}-3-oxo-2,3-diphenylpropyl)phenyl](difluoro)methylphosphonate To a solution of the product from Step 1 (54 mg, 0.10 mmol), di(t-butyl)[2-bromo-4-(bromomethyl)phenyl](difluoro)methylphosphonate (50 mg, 0.1 mmol), 18-crown-6 (10 mg), and nBu$_4$NI (cat.) in THF (1 mL) at −78° C. was added a solution of KOt-Bu (1.0 M/THF, 0.12 mL, 0.12 mmol). The reaction was allowed to warm to r.t. for 1 h, at which point it was quenched by the addition of aqueous NH$_4$OAc. After a standard aqueous workup, the crude product was purified by flash chromatography (30% EtOAc/hexane to 50% EtOAc/hexane) to yield a syrup (30 mg).

Step 3  [2-Bromo-4-(2-{4-[difluoro(phosphono)methyl]benzyl}-3-oxo-2,3-diphenylpropyl)phenyl](difluoro)methylphosphonic acid The title compound was then prepared from the product of Step 2 as described in Example 1 step 9.

$^1$H NMR (CD$_3$COCD$_3$) δ 3.42–3.59 (2H, m), 3.60–3.65 (2H, m), 6.93–7.00 (4H, m), 7.18–7.23 (2H, m), 7.28–7.50 (9H, m), 7.49–7.65 (2H, m).

Example 22

[4-(2-(1H-1,2,3-benzotriazol-1-yl)-3-{3-bromo-4-[difluoro(phosphono)methyl]phenyl}-2-phenylpropyl)phenyl](difluoro)methylphosphonic acid Step 1 benzyl-1H-benzotriazole To a solution of benzotriazole (1.2 g, 10.1 mmol) in DMF (40 mL) at r.t. was added a solution of 1M KOtBu in THF (11 mL, 11 mmol). After stirring for 30 min., benzyl bromide (2.0 g, 11.6 mmol) was added. The mixture was further stirred for 1 h, diluted with H$_2$O, and extracted with EtOAc. The EtOAc extract was washed with H$_2$O (3×), dried (MgSO$_4$) and concentrated. The residue was stirred with hexane containing small amount of Et$_2$O to give 1.2 g (57%) of the title compound as a white powder.

$^1$H NMR (Acetone-d6) δ 8.00 (d, 1H), 7.72 (d, 1H), 7.48 (m, 1H), 7.42–7.25 (6H), 5.96 (s, 2H).

Step 2  [4-(2-benzotriazol-1-yl-2-phenylethyl)phenyl]difluoromethylphosphonic acid di-tert-butyl ester To a solution of 1-benzyl-1H-benzotriazole (820 mg, 3 mmol) in THF (50 mL) at −78° C. was added a solution of 2.5M n-BuLi in hexanes (1.5 mL, 3.8 mmol). The solution turned deep blue immediately. After stirring for 5 min. at −78° C., a solution of (4-bromomethylphenyl)difluoromethylphosphonic acid di-tert-butyl ester (1.4 g, 3.4 mmol) in THF (4 mL) was added. After the deep blue color disappeared, the mixture was quenched with H$_2$O and extracted with EtOAc. The EtOAc extract was washed with brine, dried (Na$_2$SO$_4$) and concentrated. The residue was stirred with Et$_2$O to give 1.77 g (84%) of the title compound as a white solid.

Step 3  di(tert-butyl)[4-(2-(1H-1,2,3-benzotriazol-1-yl)-3-{3-bromo-4-[[di(tert-butoxy)phosphoryl](difluoro)methyl]phenyl}-2-phenylpropyl)phenyl](difluoro)methylphosphonate The title compound was prepared as described in Step 2 with the bromide of Example 18 Step 6.

Step 4  [4-(2-(1H-1,2,3-benzotriazol-1-yl)-3-{3-bromo-4-[difluoro(phosphono)methyl]phenyl}-2-phenylpropyl)phenyl](difluoro)methylphosphonic acid The compound was prepared from the product of Step 3 using the procedure of Example 1 Step 9.

$^1$H NMR (CD$_3$COCD$_3$) δ 4.10 (4H, m), 6.70–8.00 (16H, m).

Example 23

({4-[2-Benzotriazol-1-yl-3-[4-(difluoro-phosphono-methyl)-phenyl]-2-(4-methoxycarbonyl-phenyl)-propyl]-phenyl}-difluoro-methyl)-phosphonic acid Step 1  methyl 4-(1H-1,2,3-benzotriazol-1-ylmethyl)benzoate To a solution of benzotriazole (1.14 g, 9.6 mmol) in DMF (25 mL) at 0° C. was added methyl 4-bromomethylbenzoate (2.22, 9.6 mmol) and NaH (12.25 mmol, 60% in oil). After stirring for 2 h, the mixture was diluted with aqueous NH$_4$Cl, extracted with EtOAc. The EtOAc extract was washed H$_2$O (3×), dried (MgSO$_4$) and concentrated. The residue was chromatographed to give 1.32 g (51%) of the title compound as a white powder.

Step 2  (4-2-(1H-1,2,3-benzotriazol-1-yl)-2-[4-(methyloxycarbonyl)phenyl]ethylphenyl)(difluoro)methylphosphonic acid di-tert-butyl ester To a solution of methyl 4-(1H-1,2,3-benzotriazol-1-ylmethyl)benzoate (804 mg, 3 mmol) and (4-bromomethylphenyl)difluoromethylphosphonic acid di-tert-butyl ester (1.23 g, 3.0 mmol) in THF (20 mL) at −40° C. was added a solution of 1.0 M potassium tert-butoxide in THF (3.3 mL, 3.3 mmol). After stirring for 1 h at −40° C., aqueous NH$_4$Cl was added, the mixture was extracted with EtOAc. The EtOAc extract was washed with brine, dried (MgSO$_4$) and concentrated. The residue was chromatographed to give 894 mg (50%) of the title compound as a white powder.

Step 3  4-(1-benzotriazol-1-yl-1-{4-[(di-tert-butoxy-phosphoryl)-difluoromethyl]-benzyl 1-3-{4-[(di-tert-butoxy-phosphoryl)-difluoro-methyl]-phenyl}-ethyl)-benzoic acid methyl ester To a solution of the product obtained from Step 2, (120 mg, 0.2 mmol) and (4-bromomethylphenyl)difluoromethylphosphonic acid di-tert-butyl ester (82.6 mg, 0.2 mmol) in THF (2 mL) at −40° C. was added a solution of 1.0 M potassium tert-butoxide in THF (0.32 mL, 0.32 mmol). After stirring for 0.25 h at −40° C., aqueous NH₄Cl was added, the mixture was extracted with EtOAc. The EtOAc extract was washed with brine, dried (MgSO₄) and concentrated. The residue was chromatographed on silica gel (eluted with 60% EtOAc/hexane) to give 50 mg (26%) of the title compound.

Step 4 ({4-[2-benzotriazol-1-yl-3-[4-(difluoro-phosphono-methyl)-phenyl]-2-(4-methoxycarbonyl-phenyl)-propyl]-phenyl}-difluoro-methyl)phosphonic acid To a solution of the product obtained from Step 3 (50 mg, 0.053 mmol) in HOAc (1 mL) was added H₂O (0.15 mL). The mixture was stirred at r.t. for 20 h. The solvent was evaporated to give the title compound (34 mg).

$^1$H NMR (Acetone-d₆) δ 3.84 (3H, s), 3.90 (2H, d), 4.10 (2H, d), 6.68 (4H, d), 7.25 (4H, d), 7.30 (2H, m), 7.40 (3H, m), 7.86 (2H, d), 8.10 (1H, d).

Example 24

(4-(E)-2-(1H-1,2,3-Benzotriazol-1-yl)-2-[4-(methyloxycarbonyl)phenyl]-5-phenyl-4-pentenylphenyl)(difluoro)methylphosphonic acid Step 1 (4-(E)-2-(1H-1,2,3-benzotriazol-1-yl)-2-[4-(methyloxycarbonyl)phenyl]-5-phenyl-4-pentenylphenyl)(difluoro)methylphosphonic acid di-tert-butyl ester To a solution of the product obtained from Step 2, Example 23 (120 mg, 0.2 mmol) and cinnamyl (59 mg, 0.3 mmol) in THF (2 mL) at −40° C. was added a solution of 1.0 M potassium tert-butoxide in THF (0.4 mL, 0.4 mmol). After stirring for 0.5 h at −40° C., aqueous NH₄Cl was added, the mixture was extracted with EtOAc. The EtOAc extract was washed with brine, dried (MgSO₄) and concentrated. The residue was chromatographed on silica gel to give 37 mg (26%) of the title compound.

Step 2 (4-(E)-2-(1H-1,2-3-benzotriazol-1-yl)-2-[4-methyloxycarbonyl)phenyl]-5-phenyl-4-pentenylphenyl)(difluoro)methylphosphonic acid To a solution of the product obtained from Step 1 (37 mg, 0.05 mmol) in HOAc (1 mL) was added H₂O (0.15 mL). The mixture was stirred at r.t. for 20 h. The solvent was evaporated to give the title compound.

$^1$H NMR (Acetone-d₆) δ 3.55 (2H, m), 3.87 (3H, s), 4.18 (2H, q), 6.08 (1H, m), 6.35 (1H, d), 6.72 (2H, d), 6.91 (1H, d), 7.20 (4H, m), 7.35 (6H, m), 8.00 (4H, m).

Example 25

(4-2-(1H-1,2,3-Benzotriazol-1-yl)-2,3-di[4-(methyloxycarbonyl)phenyl]propylphenyl)(difluoro)methylphosphonic acid Step 1 (4-2-(1H-1,2,3-benzotriazol-1-yl)-2,3-di{4-(methyloxycarbonyl)phenyl]propylphenyl)(difluoro)methylphosphonic acid To a solution of the product obtained from Step 2, Example 23 (120 mg, 0.2 mmol) and methyl 4-bromomethylbenzoate (57 mg, 0.25 mmol) in THF (2 mL) at −40° C. was added a solution of 1.0 M potassium tert-butoxide in THF (0.4 mL, 0.4 mmol). After stirring for 1.5 h at −40° C., aqueous NH₄Cl was added, the mixture was extracted with EtOAc. The EtOAc extract was washed with brine, dried (MgSO₄) and concentrated. The residue was chromatographed on silica gel to give 85 mg (56%) of the title compound.

Step 2 {[4-(2-benzotriazol-1-yl-3-biphenyl-4-yl-2-phenyl-propyl)-phenyl]-difluoro-methyl}-phosphonic acid To a solution of the product obtained from Step 1 (85 mg, mmol) in HOAc (1 mL) was added H₂O (0.15 mL). The mixture was stirred at r.t. for 20 h. The solvent was evaporated to give the title compound.

1H NMR (Acetone-d₆) δ 3.80 (3H, s), 3.87 (3H, s), 4.01 (2H, q), 4.25 (2H, q), 6.75 (3H, t), 6.87 (2H, d), 7.25 (5H, m), 7.38 (1H, t), 7.65 (2H, d), 7.93 (2H, d), 8.02 (1H, t).

Example 26

{4-[(E)-2-Benzoyl-2,5-diphenyl-4-pentenyl]-2-fluorophenyl}(difluoro)methylphosphonic acid Step 1 2-fluoro-4-methylbenzonitrile 2-Fluoro-4-methylaniline (15 g, 120 mmol, 1 eq) was dissolved in 600 ml 1M HCl at 0° C. and a 120 ml aqueous solution of sodium nitrite (12.4 g, 180 mmol, 1.5 eq) was added dropwise, maintaining the temperature under 5° C. The solution was neutralized with solid NaHCO₃ and poured into a 600 ml aqueous solution of 36 g KCN and 23.8 g CuCN at 60° C. The solution was stirred for 30 min and cooled to RT. The product was extracted 3 times with EtOAc and the combined organic layers were washed with brine and dried with sodium sulfate. The solvent was removed and 16 g (98%) of product was obtained.

Step 2 2-fluoro-4-methylbenzoic acid

Compound of Step 1 (14 g, 105 mmol, 1 eq) was dissolved in 2-(2-ethoxyethoxy) ethanol (105 mL) and KOH (105 ml of a 8 M solution, 840 mmol, 8 eq) was added, the mixture was refluxed under nitrogen for 3 hours. The mixture was cooled and the pH set to 3. The product was extracted with EtOAc and the organic layer was washed 3 times with water and dried with sodium sulfate. The crude mixture was purified on silica using a 0–3% acetic acid/toluene gradient. 3.1 g of the desired compound (19%) was obtained.

$^1$H NMR (400 MHz, CDCl₃) δ 2.40 (3H, s), 7.00 (2H, m), 7.90 (1H, t).

Step 3 2-fluoro-4-(bromomethyl)benzoic acid

Compound of Step 2 was treated as described in Example 18 Step 1.

Step 4 [2-fluoro-4-(bromomethyl)phenyl]methanol

Compound of Step 3 was treated as described in Example 18 Step 2.

Step 5 4-(bromomethyl)-2-fluorobenzaldehyde

Compound of Step 4 was treated as described in Example 18 Step 3.

Step 6 di(tert-butyl)[4-(bromomethyl)-2-fluorophenyl](hydroxy)methylphosphonate

Compound of Step 5 was treated as described in Example 18 Step 4.

Step 7 di(tert-butyl)4-(bromomethyl)-2-fluorobenzoylphosphonate

Compound of Step 6 was treated as described in Example 18 Step 5.

Step 8 di(tert-butyl)[4-(bromomethyl)-2-fluorophenyl](difluoro)methylphosphonate Compound of Step 7 was treated as described in Example 18 Step 6.

Step 9 {4-[(E)-2-benzoyl-2,5-diphenyl-4-pentenyl]-2-fluorophenyl}(difluoro)methylphosphonic acid Compound of Step 8 was treated as described in Example 20.

$^1$H NMR (CD₃COCD₃, 400 MHz) δ 3.05 (2H, m), 3.50 (2H, m), 6.20–7.55 (20H, m).

Example 27

[4-(2-Benzoyl-2,5-diphenylpentyl)-2-bromophenyl](difluoro)methylphosphonic acid

Step 1 1,2,5-triphenyl-1-pentanone

To the compound of Example 9 Step 1 (0.20 g, 0.64 mmole) dissolved in EtOAc was added Pd/C. The reaction was then stirred for 2 h under 1 atmosphere of H$_2$, and was then filtered through celite and evaporated.

Step 2 [4-(2-Benzoyl-2,5-diphenylpentyl)-2-bromophenyl](difluoro)methylphosphonic acid The product of Step 1 was treated as described in Example 9, Step 2 and 3, to give the title compound.
M/z 611

Example 28

[4-(2-benzyl-3-oxo-2,3-diphenylpropyl)-2-bromophenyl](difluoro)methylphosphonic acid The title compound was prepared as described in Example 20 using benzyl bromide as alkylating agent instead of cinnamyl bromide.

$^1$H NMR (CD$_3$COCD$_3$, 400 MHz) δ 3.40–3.80 (4H, m), 6.90–7.95 (18H, m).

Example 29

[4-(2-benzyl-2,5-diphenylpentyl)phenyl](difluoro)methylphosphonic acid

The compound of Example 9 in EtOAc was treated with Pd/C and H2 (50 psi) for 2 days. After filtration and evaporation the title compound was obtained.

$^1$H NMR (CD$_3$COCD$_3$, 400 MHz) δ 1.50–3.20 (1OH, m), 6.50–7.50 (19H, m).

Example 30

{4-[(4E )-2-(4-cyanophenyl)-2-(4-fluorobenzoyl)-5-phenyl-4-pentenyl]phenyl}(difluoro)methylphosphonic acid The title compound was prepared using the protocol as described for Example 1, using 4-bromomethyl benzonitrile as the alkylating agent for Step 2.

$^1$H NMR (CD$_3$COCD$_3$, 400 MHz) δ 3.05–3.55 (4H, m), 6.20–7.85 (17H, m).

Example 31

(4-{2-(4-cyanophenyl)-3-(4-fluorophenyl)-3-oxo-2-[(2-phenylcyclopropyl)methyl]propyl}phenyl)(difluoro)methylphosphonic acid To 4-[(3E)-1-(4-fluorobenzoyl)-4-phenyl-3-butenyl]benzonitrile prepared following Steps 1,2 (with 4-bromomethyl benzonitrile as alylating agent) and 3 of Example 1. (0.20 g, 0.56 mmole) in ether containing an excess of CH$_2$N$_2$ was added Pd(OAc)$_2$. The reaction was then filtered over silica gel. The crude product was converted to the title compound following the procedure of Example 1 Steps 8 and 9.

$^1$H NMR (CD$_3$COCD$_3$, 400 MHz) δ 0.70–3.70 (6H, m), 6.70–7.70 (17H, m).

Example 32

{4-[(4E)-2,5-diphenyl-2-(phenylsulfonyl)-4-pentenyl]phenyl}(difluoro)methylphosphonic acid The title compound was prepared from (benzylsulfonyl)benzene in the same manner as in Example 9.

$^1$H NMR (CD$_3$COCD$_3$) δ 3.03–3.26 (2H, m), 3.90–4.08 (2H, m), 6.22–6.36 (2H, m), 7.11–7.45 (16H, m), 7.45–7.53 (2H, m), 7.58–7.67 (1H, m).

Example 33

Difluoro(4-{(4E)-2-(4-fluorobenzoyl)-2-[3-(methoxycarbonyl)phenyl]-5-phenyl-4-pentenyl}phenyl)methylphosphonic acid Step 1 methyl 3-[2-(4-fluorophenyl)-2-oxoethyl]benzoate This compound was prepared in the same manner as Example 1 Step 2; using methyl 3-(bromomethyl)benzoate to give a pale yellow solid.

Step 2 Difluoro(4-(4E)-2-(4-fluorobenzoyl)-2-[3-(methoxycarbonyl)phenyl]-5-phenyl-4-pentenyl}phenyl) methylphosphonic acid The material from Step 1 was treated in the same manner as in Example 1 Steps 3 through 9 to give the title compound as a pale yellow syrup.

$^1$H NMR (CD$_3$COCD$_3$) δ 3.0–3.14 (2H, m), 3.48–3.54 (2H, m), 3.83 (3H, s), 6.12–6.22 (2H, m), 6.78–6.76 (2H, m), 7.02–7.12 (2H, m), 7.12–7.49 (7H, m), 7.49–7.58 (1H, m), 7.58–7.66 (2H, m), 7.79–7.85 (1H, m), 7.94–8.00 (1H, m).

Example 34

Difluoro(4-{(E)-2-(4-fluorophenyl)sulfonyl]-2-[4-(methoxycarbonyl)phenyl]-5-phenyl-4-pentenyl}phenyl)methylphosphonic acid Step 1 methyl 4-1((4 fluophenyl)sulfanyl]methyl}benzoate To a solution of p fluorothiophenol (2.0, 15.6 mmole) in DMF at 0° C. was added NaH (0.49 g, 15 mmole). The reaction was stirred for 10 minutes. Then a solution of methyl 4-(bromomethyl)benzoate (3.57 g, 15.6 mmole) in THF (5 mL) was added to the mixture at room temperature and stirred for 1 hour. The reaction was quenched with saturated NH$_4$Cl to give a precipitate and filtered, air dried to yield 4.0 g of the title compound.

Step 2 methyl 4-{[(4-fluorophenyl)sulfonyl]methyl}benzoate

To a solution of methyl4-{[(4-fluorophenyl)sulfanyl]methyl}benzoate (4 g, 14.47 mmole) in CH$_2$Cl$_2$/MeOH 10:1 at 0° C. was added MMPP (7.5 g, 14.47 mmole) portion wise. The reaction was then stirred at r.t for 40 minutes. The mixture was filtered through a pad of silica gel, and the organic phase was washed with NaHCO$_3$ saturated solution, dried and evaporated. The residue was chromatographed using hexane/ethyl acetate 20% to yield 0.26 g of the desired product.

Step 3 methyl 4-{(E)-1-[(4-fluorophenyl)sulfanyl]-4-phenyl-3-butenyl}benzoate

To a solution of methyl 4-{[(4-fluorophenyl)sulfonyl]methyl}benzoate (0.26 g, 0.84 mmole) in DMF at 0° C. was added NaH (25 mg, 0.74 mmole) and the reaction was stirred for 15 minutes at 0° C. Then a solution of cinnamyl bromide (0.16 g, 0.81 mmole) in THF (1 mL) was added, and the reaction was allowed to warm to room temperature. The reaction was quenched with saturated NH$_4$Cl solution and extracted with ethyl acetate. The organic phase was dried (Na$_2$SO$_4$), filtered, and evaporated. The residue was chromatographed to yield 0.35 g of the title compound.

Step 4 methyl 4-{(E)-1-{4-[[di(tert-butoxy)phosphoryl](difluoro)methyl]benzyl}-1-[(4-fluorophenyl)sulfonyl]-4-phenyl-3-butencyl}benzoate To a solution of methyl 4-{(E)-1-[(4-fluorophenyl)sulfonyl]-4-phenyl-3-butenyl}benzoate (0.35 g, 0.84 mmol) in THF (3 mL) at –78° C. was added potassium tert-butoxide (840 μL, 0.84 mmole), followed by di(tert-butyl)[4-(bromomethyl)phenyl]difluoro methyl phosphonate (0.35 g, 0.84 mmole). The reaction was then allowed to warm slowly to room temperature. The reaction mixture was stirred 1 hour, quenched with saturated NH₄Cl solution and extracted with ethyl acetate. The organic phase was dried (Na₂SO₄), filtered, and evaporated. The residue was chromatographed to yield 0.2 g of the corresponding ester.

Step 5 Difluoro(4-{(E)-2-(4-fluorophenyl)sulfonyl]-2-[4-(methoxycarbonyl)phenyl]-5-phenyl-4-pentenyl}phenyl)methylphosphonic acid The ester of Step 4 was hydrolysed as in Example 1 Step 9.

$^1$H NMR (300 MHz, acetone d₆) δ 3.1–3.4 (2H, m), 3.9 (3H, s), 3.92–4.1 (2H, q), 6.3 (2H, m), 7.1–7.3 (9H, m), 7.42 (4H, m), 7.65 (2H, d), 7.9 (2H, d).

Example 35

(4-{(E)-2-[(5-bromo-3-pyridinyl)carbonyl]-2-[4-(methylsulfanyl)phenyl]-5-phenyl-4-pentenyl}phenyl)(difluoro)methylphosphonic acid Step 1 1-(5-Bromopyridin-3-yl-2-(4-methylsulfanylphenyl)-ethanone To SOCl₂ (100 mL) at r.t. was added 5-bromonicotinic acid (6.2 g, 30.7 mmol) and the mixture was refluxed for 3 h. A homogeneous solution resulted after 2 h. Excess SOCl₂ was removed in vacuo to give the acid chloride intermediate.

To N,O-dimethylhydroxylamine hydrochloride (6.0 g, 61.5 mmol) in CH₂Cl₂ (100 mL) was added pyridine (10 mL) at 0° C. followed by a solution of above acid chloride in CH₂Cl₂. The mixture was stirred at 0° C. for 1 h., washed with H₂O (3×), concentrated and dried under vacuum to give the corresponding amide (7.4 g, 98%) as a light brown oil.

To Mg turning (4.5 g) in Et₂O (60 mL) with a few small crystals of I₂ at r.t. was added dropwise 4-(methylthio)benzyl chloride over a period of ~30 min. The resulting Grignard reagent was cooled to 0° C. and a solution of above amide in THF (100 mL) was added. After stirring for 30 min., the mixture was quenched with H₂O (150 mL+4 mL of HOAc), extracted with EtOAc. The EtOAc extract was washed with brine (2×), dried (anhydrous MgSO₄) and concentrated. Chromatography over silica gel and elution with hexanes:EtOAc, followed by (5:2) stirring with Et₂O gave the title compound as a white powder (2.6 g, 27%).

Step 2 (E)-1-(5 bromo-3-pyridinyl)-2-[4-(methylsulfanyl)phenyl]-5-phenyl-4-penten-1-one To 1-(5-bromo-3-pyridinyl)-2-[4-(methylsulfanyl)phenyl]-1-ethanone in DMF (2.5 mL) at 0° C. was added NaH (15 mg, 0.5 mmole). The reaction was stirred 30 minutes, at which point cinnamyl bromide (0.1 g, 0.5 mmole) was added and the reaction was allowed to warm to room temperature. The reaction was quenched with H₂O and extracted with ethyl acetate. The organic phase was dried (Na₂SO₄), filtered, and evaporated to give the title compound.

Step 3 di(tert-butyl)(4-{(E)-2-[(5-bromo-3-pyridinyl)carbonyl]-2-[4-(methylsulfanyl)phenyl]-5-phenyl-4-pentenyl}phenyl)(difluoro)methylphosphonate To a solution of (E)-1-(5-bromo-3-pyridinyl)2-[4-(methylsulfanyl)phenyl]-5-phenyl-4-penten-1-one (0.2 g, 0.5 mmole, 18 Crown-6 (15 mg) tetrabutyl ammonium iodide (catalytic amount) in degassed THF (10 mL) at −78° C. was added potassium tert-butoxide (0.5 mL, 1M solution) dropwise. The reaction was stirred for 10 minutes, then di(tert-butyl)[4-(bromomethyl)phenyl](difluoro) methylphosphonate (0.2 g, 0.5 mmole) was added. The reaction was brought to room temperature for 1 hour and was then quenched with saturated NH₄Cl solution and extracted with ethyl acetate. The organic phase was dried (Na₂SO₄), filtered, and evaporated. The residue was purified by flash chromatography, to give the title compound.

Step 4

The ester from Step 2 was hydrolysed by treatment with 9:1 AcOH/H₂O overnight at room temperature. The mixture was evaporated to dryness, and co-distilled with toluene to give 0.02 g of the title product.

$^1$H NMR (300 MHz) acetone d₆) δ 2.52 (3H, s), 2.99 (2H, m), 3.42–3.64 (2H, q), 6.2 (2H, m), 6.85 (2H, d), 7.15–7.45 (11H, m), 7.95 (1H, s), 8.45 (1H, m), 8.75 (1H, m).

Example 36

(4-{(E)-2-benzoyl-2-[4-(3-methyl-1,2,4-oxadiazol-5-yl)phenyl]-5-phenyl-4-pentenyl}phenyl)(difluoro)methylphosphonic acid Step 1 4-(2,2-dimethoxy-2-phenylethyl)benzoic acid To a solution of methyl 4(2-oxo-2-phenylethyl)benzoate (1 g, 3.9 mmole) in MeOH (40 mL) was added trimethylorthoformate 10 mL and CSA (50 mg). The reaction mixture was refluxed for 6 h. The mixture was cooled, then Et₃N (0.5 mL) was added, and the mixture concentrated. The residue was dissolved in THF and stirred overnight. The reaction was quenched with ACOH (1 mL) and 40 mL pH 7 phosphate buffer. The organic phase was dried (Na₂SO₄), filtered, and evaporated to yield the title compound 1.1 g.

Step 2 2-[4-(3-methyl-1,2,4-oxadiazol-5yl)phenyl]-1-phenyl-1-ethanone

To 4-(2,2-dimethoxy-2-phenylethyl)benzoic acid (1.1 g, 3.84 mmole) in DMF (15 mL) was added carbonyldiimidazole (0.68 g, 4.2 mmole). After 20 min, N-hydroxy ethanimidamide (0.33 g, 4.5 mmole) was added and the mixture stirred for 45 min. at r.t. followed by 100° C. overnight. The reaction was cooled, poured in H₂O (30 mL) and extracted with hexane/ethylacetate 1:1. The organic phase was dried over Na₂SO₄ and concentrated. The residue was dissolved in 100 mL acetone and treated with p-toluene sulfonic acid (100 mg) for 2 h. Et₃N (0.5 mL) was added, and the mixture was concentrated to dryness. The residue was dissolved in 2:1 hexane/ethyl acetate (10 mL) and passed through a pad of silica gel, eluting with 1: 1 hexane:EtOAc. The fractions were concentrated, and the residue was stirred with 4:1 hexane:EtOAc 10 mL to give 0.49 g of the desired compound.

Step 3 (E)-2-[4-(3-methyl-1,2,4-oxadiazol-5-yl)phenyl]-1,5-diphenyl-4-penten-1-one To a solution of 2-[4-(3-methyl-1,2,4-oxadiazol-5-yl)phenyl]-1-phenyl 1-ethanone (0.2 g, 0.72 mmole) in DMF (3 mL) was added NaH (0.022 g, 0.7 mmole) at 0° C. The reaction was stirred for 15 min. Then a solution of cinnamyl bromide (0.16 g, 0.84 mmol) in 1 mL DMF was added. The reaction was warmed to room temperature, and was then quenched with saturated NH₄Cl solution and extracted with ethyl acetate. The organic phase was then dried (Na₂SO₄), filtered, and evaporated to give the title compound.

Step 4 di(tert-butyl)(4-{(E)-2-benzoyl-2-[4-(3-methyl-1,2,4-oxadiazol-5-yl)phenyl]-5-phenyl-4-pentenyl}phenyl)(difluoro)methylphosphonate To a solution of (E)-2-[4-(3-methyl-1,2,4-oxadiazol-5-yl)phenyl]-1,5-diphenyl-4-penten-1 one (0.35 g, 0.84 mmole) in THF (3 ML) was added a solution of potassium tert-butoxide (0.84 mL, 1M) at −78° C. followed by di(tert-butyl)[4-(bromomethyl)phenyl](difluoro)methylphosphonate (0.35 g, 0.84 mmole). The reaction was allowed to warm to room temperature for 1 hour, and was then quenched with saturated NH₄Cl solution and extracted with ethyl acetate. After drying over Na₂SO₄ and removal of solvent, the residue was chromatographed using hexane/EtOAc 30% yielding 0.2 g of the corresponding ester.

Step 5

The ester from Step 4 was hydrolysed as in Example 35 Step 3.

$^1$H NMR (300 MHz) acetone d$_6$ δ 2.42 (3H, s), 3.1 (2H, m), 3.52–3.68 (2H, q), 6.2 (2H, s), 6.8 (2H, d), 7.15–7.40 (9H, m), 7.50 (3H, m)m 7.58 (2H, d), 8.14 (2H, d).

Example 37

(4-{2-{4-[difluoro(phosphono)methyl]benzyl}-3-(4-fluorophenyl)-2-[4-(methoxycarbonyl)phenyl]-3-oxopropyl}-1,1'-biphenyl(4-{2-([1,1'-biphenyl]-4-ylmethyl)-3-(4-fluorophenyl)-2-[4-(methoxycarbonyl)phenyl]-3-oxopropyl}phenyl)(difluoro)methylphosphonic acid Step 1 methyl 4-[1-[1,1'-biphenyl]-4-ylmethyl)-2-(4-fluorophenyl)-2-oxoethyl]benzoate To a solution of methyl 4-[2-(4-fluorophenyl)-2-oxoethyl]benzoate (from Example 1, Step 2) (0.2 g, 0.73 mmole) in DMF (2 mL) at 0° C. was added NaH (22 mg, 0.65 mmole), After stirring for 10 minutes, 4-bromomethyl biphenyl (0.18 g, 0.73 mmole) was added to the solution. The reaction was allowed to warm to r.t. and was then quenched by the addition of saturated NH$_4$Cl solution. The product was extracted with EtOAc and the organic phase was dried (Na$_2$SO$_4$), filtered, and evaporated. Purification by flash chromatography gave the product as a syrup (0.2 g).

Step 2 methyl 4-[1-([1,1'-biphenyl]-4-ylmethyl)-1-{4-[[di(tert-butoxy)phosphoryl](difluoro)methyl]benzyl}-2-(4-fluorophenyl)-2-oxoethyl]benzoate To a solution of methyl 4-([1-1'-biphenyl]-4-ylmethyl)2-(4-fluorophenyl)-2-oxoethyl)benzoate (0.2 g, 0.45 mmole), 18-Crown-6 (36 mg), and tetrabutylammonium iodide (catalytic amount) in degassed THF (3 mL) at −78° C. was added pottasium tert-butoxide (0.46 mL, 0.46 mmole). The reaction was stirred for 10 minutes then di(tert-butyl)[4-(bromomethyl)phenyl](difluoro)phosphonate (0.18 g, 0.43 mmole) was added. The reaction was allowed to warm to room temperature, and was then quenched with saturated NH$_4$Cl solution and extracted with ethyl acetate. After drying (Na$_2$SO$_4$), filtering, and removal of solvent, the residue was purified by chromatography to give the corresponding ester. Step 5 hydrolysis was carried out as in Example 35, Step 3 to give 70 mg of the title compound.

$^1$H NMR (300 MHz, NMR) acetone d$_6$ δ 3.55–3.72 (3H, m), 3.72–3.9 (1H, m), 3.86 (3H, s), 6.82 (2H, d), 7.0–7.50 (12H, m), 7.5–7.72 (5H, m), 7.94 (2H, d).

Example 38

Difluoro(4-{3-(4-fluorophenyl)-2-[4-(methoxycarbonyl)phenyl]-3-oxo-2-[(2-phenylcyclopropyl)methyl]propyl}phenyl)methylphosphonic acid Step 1 methyl 4-[(E)-1-(4-fluorobenzoyl)-4-phenyl-3-butenyl]benzoate To a solution of methyl 4-[2-((4-fluorophenyl)-2-oxoethyl]benzoate (Example 1, Step 2) (1.0 g, 3.67 mmole) in DMF (10 mL) at 0° C. was added NaH (0.105 mg, 3.6 mmol). After stirring for 10 minutes at 0° C., cinnamyl bromide (0.71 g, 3.6 mmole) was added to the mixture. The reaction was stirred for r.t. for 1 h. and was then quenched with saturated ammonium chloride and extracted with ethyl acetate. The organic phase dried (Na$_2$SO$_4$), filtered, and evaporated. The residue was purified by flash chromatography to yield 1.02 g of the desired product.

Step 2 methyl 4-{2-(4-fluorophenyl)-2-oxo-1-[(2-phenylcyclopropyl)methyl]ethyl}benzoate To a solution of methyl 4-[(E)-1-(4-fluorobenzoyl)-4-phenyl-3-butenyl benzoate (0.18 g, 0.464 mmole) dissolved at 0° C. in a diazomethane/Et$_2$O excess solution was added Pd (OAc)$_2$ (5 mg). The reaction was stirred for 10 minutes, and evaporated to dryness. The residue was purified by flash chromatography (30% EtOAc:hexane) to give 50 mg of the desired compound.

Step 3 methyl 4-{1-4-[[di(tert-butoxy)phosphoryl](difluoro)methyl]benzyl}-2-(4-fluorophenyl)-2-oxo-1-[(2-phenylcyclopropyl)methyl]ethyl}

To a solution of methyl 4-{2-(4-fluorophenyl)-2-oxo-1-[2-phenylcyclopropyl)methyl]ethyl}benzoate (0.05 g, 0.124 mmole), 18 Crown −6 (15 mg), and tetrabutylammonium iodide (catalytic amount) in degassed THF (2 mL) at −78° C. was added potassium tert-butoxide (0.124 mL, 1M in THF). The mixture was stirred 10 minutes, and then di(tert-butyl)[4-(bromomethyl)phenyl](difluoro)methylphosphonate (5 mg, 0.123 mmole) was added. The reaction was allowed to warm to room temperature, was then quenched with saturated NH$_4$Cl solution and extracted with ethyl acetate. The organic phase was dried (Na$_2$SO$_4$), filtered, and evaporated. The residue was purified by flash chromatography to yield the corresponding ester.

Step 4

The ester was hydrolysed with a mixture of 9:1 ACOH/H$_2$O to yield 0.026 g of the title compound.

$^1$H NMR (300 MHz, NMR) acetone d$_6$ δ 0.6–1.48 (3H, m), 2.0–2.35 (2H, m), 2.6 (1H, m), 3.35–3.7 (2H, m), 3.89 (3H, s), 6.68–7.4 (11H, m), 7.4–7.7 (4H, m), 7.82 (2H, t).

Example 39

2-Chloro-4-[3-(phenyl)-2-methyl-3-oxo-2-phenylpropyl]phenyl}(difluoro)methyl phosphonic acid Step 1 2-chloro-4-methyl benzonitrile The title compound was prepared as described in Example 26 Step 1 using 2-chloro-4-methylaniline.

Step 2 2-chloro-4-methylbenzoic acid

The title compound was prepared as described in Example 26 Step 2.

Step 3 2-chloro-4-(bromomethyl)benzoic acid

Compound of Step 2 was treated as described in Example 18 Step 1.

Step 4 [2-chloro-4-(bromomethyl)phenyl]methanol

Compound of Step 3 was treated as described in Example 18 Step 2.

Step 5 4-(bromomethyl)-2-chlorobenzaldehyde

Compound of Step 4 was treated as described in Example 18 Step 3.

Step 6 di(tert-butyl)[4-(bromomethyl)-2-chlorophenyl](hydroxy)methylphosphonate

Compound of Step 5 was treated as described in Example 18 Step 4.

Step 7 di(tert-butyl)4-(bromomethyl)-2-chlorobenzoylphosphonate

Compound of Step 6 was treated as described in Example 18 Step 5.

Step 8 di(tert-butyl)[4-(bromomethyl)-2-chlorophenyl](difluoro)methylphosphonate Compound of Step 7 was treated as described in Example 18 Step 6.

Step 9

The title compound was prepared as described in Example 1, Steps 8 and 9 using 1,2-diphenyl-1-propanone (Example 19, Step 1) and the alkylating agent of Step 8.

$^1$H NMR (CO$_3$COCD$_3$) δ 1.60 (3H, s), 3.45 (2H, m), 6.60–7.50 (13H, m).

Example 40

{[[{4-[(4E)-2-benzoyl-2,5-diphenyl-4-pentenyl]-2-bromophenyl}(difluoro)methyl(hydroxy)phosphoryl]oxy}methyl pivalate Step 1 disilver{4-[(4E)-2-benzoyl-2,5-diphenyl-4-pentenyl]-2-bromophenyl}(difluoro)methylphosphonate To a solution of the title compound of Example 20 (0.22 g, 0.37 mmol) in EtOH (6 mL) at r.t. was added silver trifluoroacetate (0.16 g, 0.73 mmol). After stirring for 1 h in the dark, the solvent was removed under vacuum and the residue was co-evaporated with EtOH, toluene, CH$_3$CN and Et$_2$O. The residue was stirred in Et$_2$O for 30 min. to give, after filtration, an off-white solid (0.3 g).

Step 2 {[[{4-[(4E)-2-benzoyl-2,5-diphenyl-4-pentenyl]-2-bromophenyl}(difluoro)methyl(hydroxy)phosphoryl]oxy}methyl pivalate To a suspension of the Ag salt from Step 1 (0.15 g, 0.18 mmol) in CH$_3$CN at r.t. was added iodomethyl pivalate (0.13 g, 0.54 mmol). The resulting suspension was stirred ON at r.t. The solvent was then evaporated and the residue was purified by flash chromatography, eluting with 1:10 MeOH:CH$_2$Cl$_2$ to give a pale yellow foam (26 mg).

$^1$H NMR (acetone d$_6$) δppm 1.1 (9H, s), 2.83–3.04 (2H, m), 3.32–3.46 (2H, m), 5.45–5.57 (2H, m), 6.04–6.16 (2H, m), 6.67–6.83 (2H, m), 7.14–7.25 (8H, m), 7.25–7.32 (2H, m), 7.32–7.41 (3H, m), 7.42–7.53 (3H, m).

Example 41

{[[[(2-bromo-4-{2-[4-(difluoro{hydroxy[((isobutyryloxy)methoxy]phosphoryl}methyl)benzyl]-3-oxo-2,3-diphenylpropyl}phenyl)(difluoro)methyl](hydroxy)phosphoryl]oxy}methyl 2-methylpropanoate To a solution of [2-bromo-4-(2-{4-[difluoro(phosphono)methyl]benzyl}-3-oxo-2,3-diphenylpropyl)phenyl](difluoro)methylphosphonic acid (0.16 g, 0.26 mmole) in acetonitrile (10 mL) was added chloro methyl 2-methyl propanoate (0.15 g, 1.1 mmole) and cesium carbonate (0.36 g, 1.1 mmole). The reaction mixture was refluxed overnight, and was then evaporated to dryness. The residue was purified by flash chromatography using CH$_2$Cl$_2$ and a gradient of methanol 2% to 15% yielding the title compound 0.06 g.

$^1$H NMR (400 MHz, methanol d4) δ 7.1–7.6 (13H, m), 6.88 (4H, m), 5.42 (4H, m), 3.55 (4H, m), 2.55 (2H, m), 1.15 (12H, d).

Example 42

{[[[(4-(2-{4-[(bis{[(2,2-dimethylpropanoyl)oxy]methoxy}phosphoryl)(difluoro)methyl]-3-bromobenzyl}-3-oxo-2,3-diphenylpropyl)phenyl](difluoro)methyl](hydroxy)phosphoryl]oxy}methyl pivalate To a solution of [2-bromo-4-(2-{4-[difluoro(phosphono)methyl]benzyl}-3-oxo-2,3-diphenylpropyl)phenyl](difluoro)methylphosphonic acid (0.6 g, 0.84 mmole) in acetonitrile (24 mL) was added cesium carbonate (1.19 g, 3.6 mmole) and chloromethyl pivalate (1.29 g, 8.4 mmole).

The reaction mixture was refluxed overnight, and was then cooled and poured into water, acidified with HCl 1N and extracted with ethyl acetate. The organic phase was dried (Na$_2$SO$_4$), filtered, and evaporated. The residue was flash chromatographed using CH$_2$Cl$_2$, then with a gradient of 2% to 10% methanol yielding 0.09 g $^1$H NMR (400 MHz, methanol d4) δ 6.8–7.55 (17H, m), 5.3–5.7 (6H, m), 3.32–3.62 (4H, m), 1.12 (27H, s).

Example 43

{[[[(2-bromo-4-(2-{4-[[{[(2,2-dimethylpropanoyl)oxy]methoxy}(hydroxy)phosphoryl](difluoro)methyl]benzyl}-3-oxo-2,3-diphenylpropyl)phenyl](difluoro)methyl](hydroxy)phosphoryl]oxy}methyl pivalate Obtained from the chromatography of previous example 0.1 g.

$^1$H NMR (400 MHz, methanol d$_4$) δ 7.08–7.58 (13H, m), 6.84 (4H, m), 5.42 (4H, m), 3.55 (4H, m), 1.18 (18H, s).

What is claimed is:

1. A compound represented by formula I:

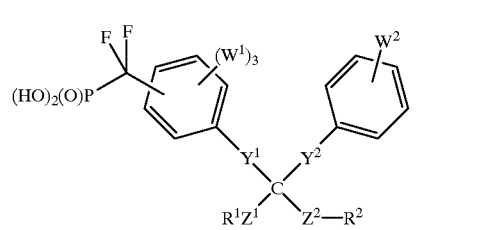

or a pharmaceutically acceptable salt or prodrug thereof, wherein:

R$^1$ is phenyl or C$_{1-6}$ alkyl, wherein said R$^1$ is optionally substituted with 1–7 substituents independently selected from —C(O)OH, SC$_{1-3}$alkyl, CN, halogen, —C(O)OC$_{1-6}$alkyl(R$^c$)$_{0-3}$, —C(O)NR$^a$R$^b$, OC$_{1-6}$alkyl (R$^c$)$_{0-3}$, C$_{1-6}$alkyl(R$^c$)$_{0-3}$, C(O)C$_{1-6}$alkyl(R$^c$)$_{0-3}$, —NHC(O)C$_{1-4}$alkyl(R$^c$)$_{0-3}$, NHC(O)NHC$_{1-4}$alkyl (R$^c$)$_{0-3}$, and —NHC(O)NH—Ar, wherein Ar is phenyl, wherein said Ar is optionally substituted with 1–3 substituents independently selected from halogen, C$_{1-3}$alkyl, C$_{1-3}$fluoroalkyl, OC$_{1-3}$alkyl, and OC$_{1-3}$fluoroalkyl;

R$^a$ and R$^b$ are each independently selected from the group consisting of H and C$_{1-4}$alkyl;

Each R$^c$ is independently selected from a group consisting of OH, OC$_{1-3}$alkyl, OC$_{1-3}$haloalkyl, C$_{0-6}$alkylene CO$_2$H, Aryl, and Aryl substituted with 1–3 substituents independently selected from halogen, C$_{1-4}$alkyl, C$_{1-4}$haloalkyl, OC$_{1-4}$alkyl, and OC$_{1-4}$haloalkyl;

R$^2$ is phenyl, R$^2$ being optionally substituted with 1–3 halogens;

Z$^1$ is a bond;

Z$^2$ is —C(O)—, S, SO, SO$_2$, CH$_2$, or a bond;

Y$^1$ and Y$^2$ are each a bond or an aliphatic linear or branched hydrocarbon group having from 1–8 carbon atoms and 0–4 double bonds, and an optional cycloalkyl group having 3–6 carbon atoms as part of said hydrocarbon group;

each W$^1$ is independently selected from H and halogen;

W$^2$ is selected from the group consisting of H, —OCF$_2$CO$_2$H, —CF$_2$PO$_3$H$_2$, —C(O)OC$_{1-6}$alkyl, and Ar, wherein Ar is optionally substituted with 1–3 substituents independently selected from halogen, $C_{1-3}$alkyl, $C_{1-3}$fluoroalkyl, $OC_{1-3}$alkyl, and —$OC_{1-3}$ fluoroalkyl;

with the proviso that when all $W^1$ groups are H, $R^1$ is phenyl, $R^2$ is phenyl and $Y^1$ and $Y^2$ are $CH_2$, then one or both of $R^1$ and $R^2$ are substituted, and $R^1$, if substituted, is substituted with a substituent other than fluorine or —$SCH_3$.

2. A compound of Formula I as recited in claim 1, wherein:

$Y^1$ is —$CH_2$—, $Y^2$ is $C_{1-3}$alkylene or $C_{2-3}$alkenylene;

and $R^1$, $R^2$, $Z^1$, $Z^2$, $W^1$, $W^2$, $R^a$, $R^b$, $R^c$, and any provisos are as defined in claim 1.

3. The compound of Formula I as recited in claim 1, wherein $R^1$ is phenyl which is optionally substituted with one substituent selected from —C(O)OH, —C(O)$OC_{1-4}$ alkyl, —NHC(O)NH—$C_6H_3(CH_3)_2$, and —C(O) $NR^aR^b$, wherein $R^a$ and $R^b$ are each independently selected from H and $C_{1-4}$alkyl;

$R^2$ is phenyl which is optionally substituted with one halogen;

$Y^1$ is $CH^2$;

$Y^2$ is —$CH_2CH=CH_2$— or —$CH_2$—;

$W^2$ is selected from the group consisting of H, —$OCF_2C$ (O)OH, —$CF_2PO_3H_2$, and —C(O)$OCH_3$;

and $Z^1$, $Z^2$, $W^1$, $R^a$, $R^b$, $R^c$, and any provisos are as defined in claim 1.

4. A compound as recited in claim 1, wherein:

$R^1$ is phenyl which is optionally substituted with —C(O) $OC_{1-4}$alkyl;

$R^2$ is phenyl which is optionally substituted with one halogen;

$Z^1$ is a bond;

$Z^2$ is —C(O)—;

$Y^1$ is —$CH_2$—;

$Y^2$ is —$CH^2CH=CH_2$—;

$W^1$ is H or a single halogen on the aromatic ring in a position adjacent to —$CF_2PO_3H_2$; and $W^2$ is H.

5. A compound as recited in claim 1, wherein:

$R^1$ is phenyl which is optionally substituted with one substituent selected from (1) —C(O)O—$C_{1-4}$alkyl, (2) —NHC(O) NH-aryl, where aryl is phenyl which is optionally substituted with 1–3 substituents independently selected from $C_{1-3}$alkyl and halogen, and (3) —C(O)N $R^aR^b$, wherein $R^a$ and $R^b$ are each independently selected from H and $C_{1-3}$alkyl;

$R^2$ is phenyl which is optionally substituted with one halogen;

$Z^1$ is a bond;

$Z^2$ is —C(O)—;

$Y^1$ is —$CH_2$—;

$Y^2$ is —$CH_2$— or a bond;

$W^1$ is H or a halogen atom on the aromatic ring in a position adjacent to —$CF_2PO_3H_2$; and $W^2$ and any provisos are as defined in claim 1.

6. A pharmaceutical composition which is comprised of a compound in accordance with claim 1 in combination with a pharmaceutically acceptable carrier.

7. A pharmaceutical composition in accordance with claim 6, further comprising an anti-diabetic or anti-obesity effective compound in addition to a compound of claim 1.

8. A method of treating diabetes in a mammalian patient in need of such treatment comprising administering to said patient an anti-diabetic effective amount of a compound in accordance with claim 1.

9. A method of treating obesity in a mammalian patient in need of such treatment comprising administering to said patient an anti-obesity effective amount of a compound in accordance with claim 1.

10. A method in accordance with claim 8, further comprising administering to said patient an anti-diabetic compound or an anti-obesity compound in addition to a compound of claim 1 in an amount effective to treat diabetes or obesity.

11. A method in accordance with claim 9, further comprising administering to said patient an anti-obesity compound or an anti-diabetic compound in an amount effective to treat obesity or diabetes.

12. A pharmaceutical composition in accordance with claim 6 further comprising an HMG-CoA reductase inhibitor.

13. A method in accordance with claim 8, further comprising administering to said patient an effective amount of an HMG-CoA reductase inhibitor.

14. A method for treating atherosclerosis in a mammalian patient in need of such treatment comprising administering to said patient an effective amount of a compound of claim 1 and an effective amount of an HMG-CoA reductase inhibitor.

15. A pharmaceutical composition (1) a compound of claim 1, (2) one or more pharmaceutically active compounds selected from the group consisting of an HMG-CoA reductase inhibitor, an anti-obesity agent, and an anti-diabetic agent, and (3) a pharmaceutically acceptable carrier.

16. A pharmaceutical composition comprising:
(1) a compound of claim 1,
(2) one or more pharmaceutically active compounds selected from the group consisting of:
(a) insulin sensitizers;
(b) PPAR-gamma agonists;
(c) biguanides;
(c) insulin or insulin mimetics;
(e) sulfonylureas;
(f) alpha-glucosidase inhibitors;
(g) cholesterol lowering agents;
(h) PPAR alpha-gamma agonists;
(i) antiobesity compounds;
(j) ileal bile acid transporter inhibitors; and
(k) insulin receptor activators; and
(3) a pharmaceutically acceptable carrier.

17. A compound according to claim 1, or an enantiomer or a pharmaceutically acceptable salt thereof, having a structure selected from the group consisting of:

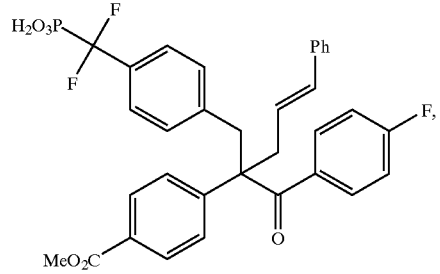

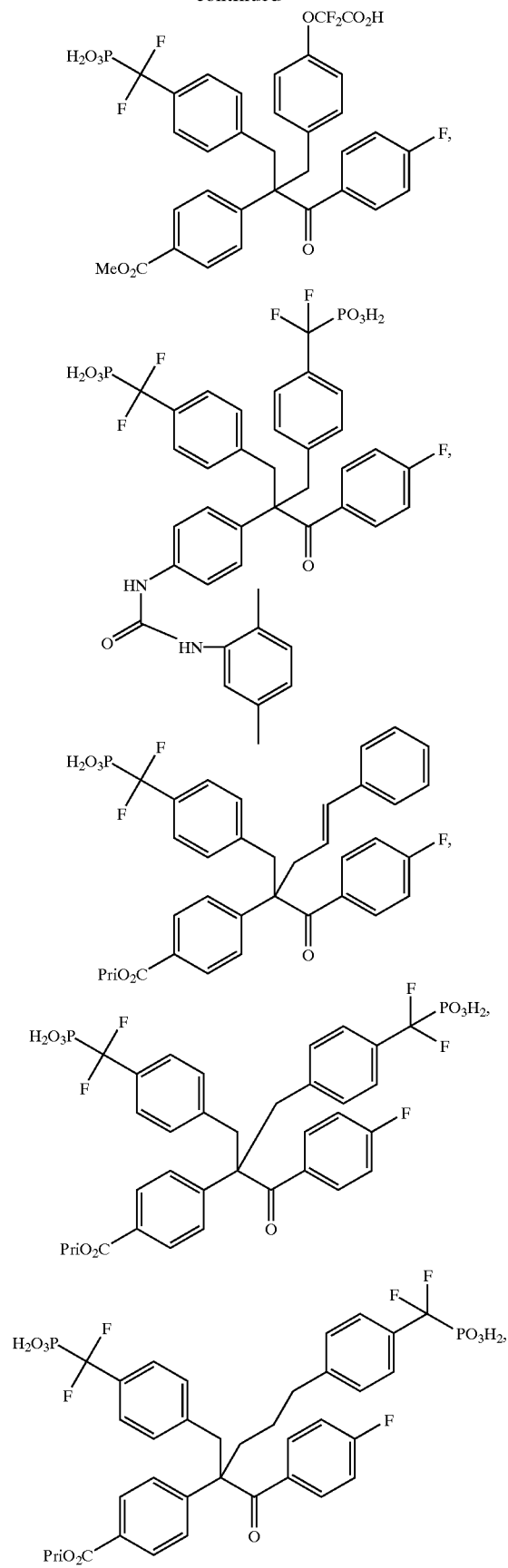
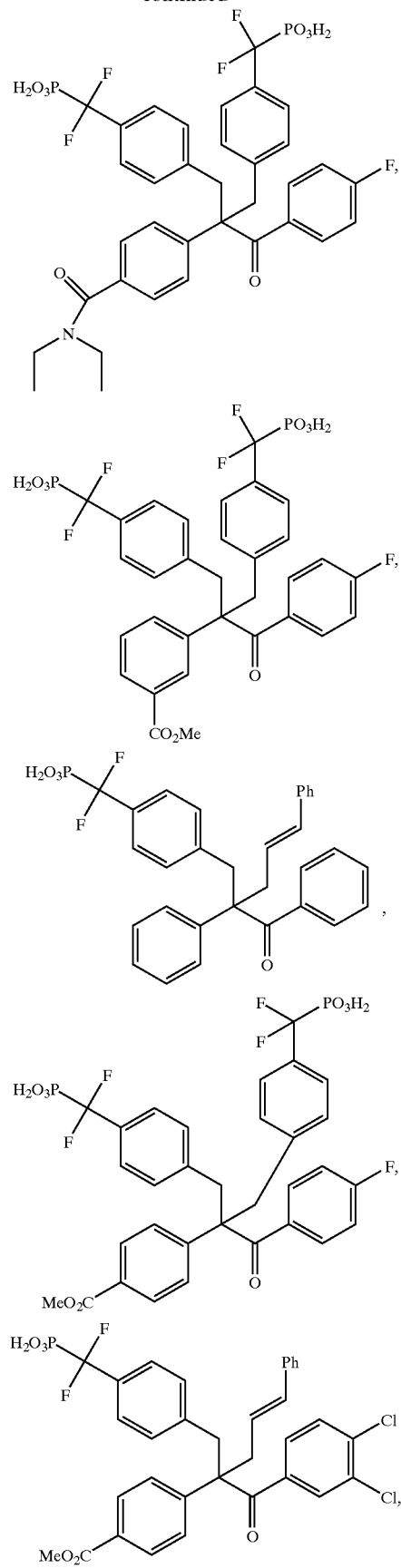

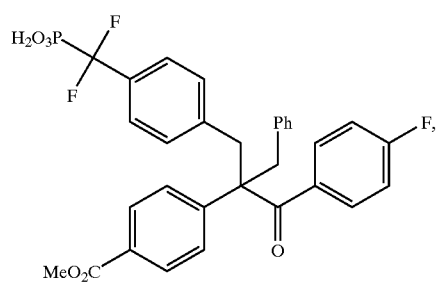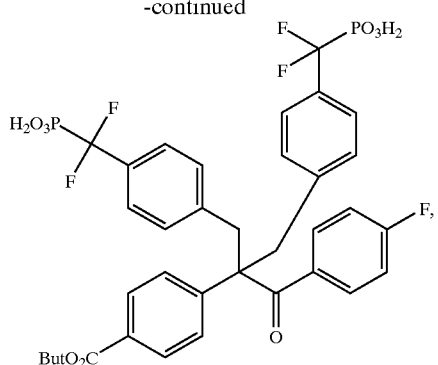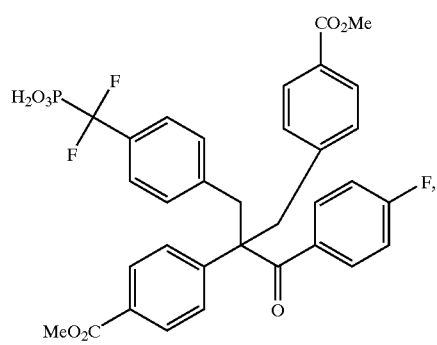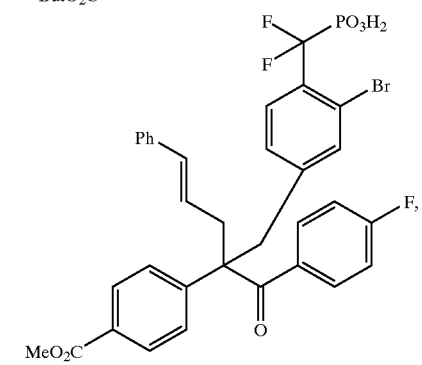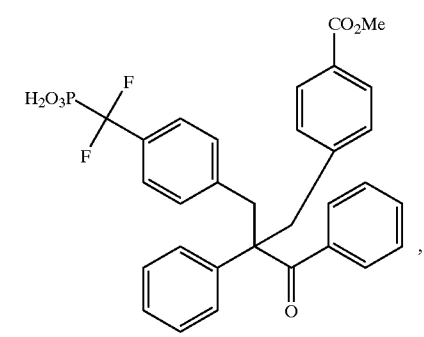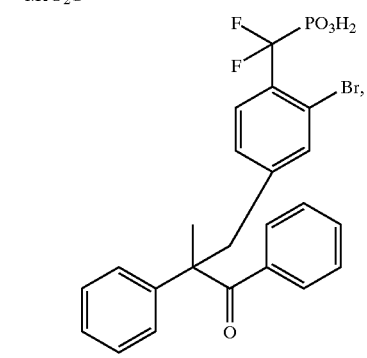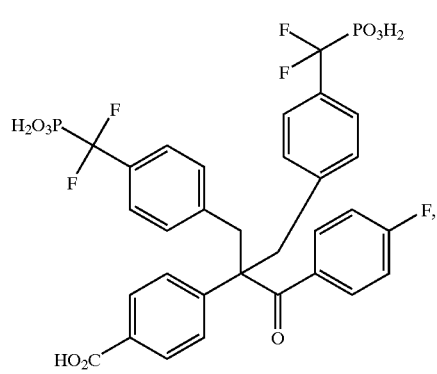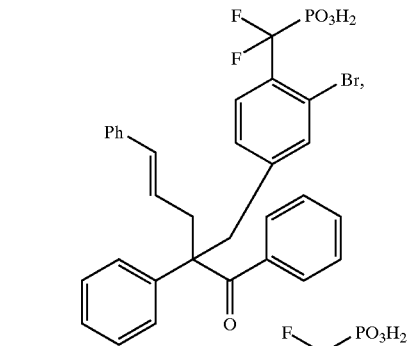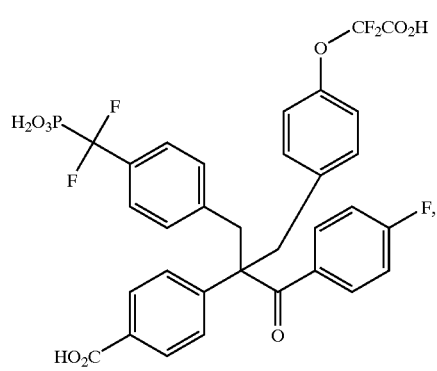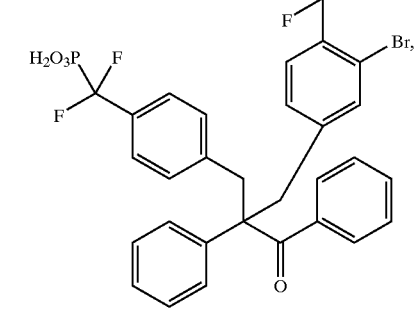

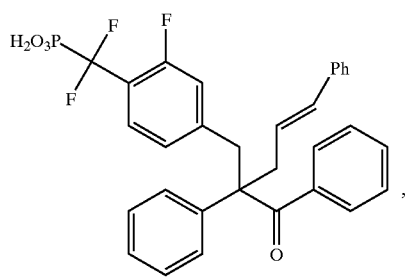
,
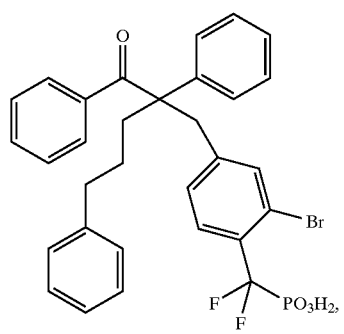
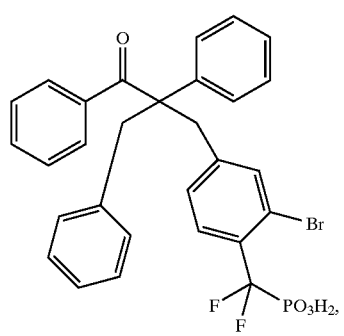
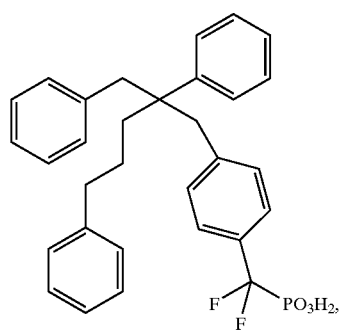
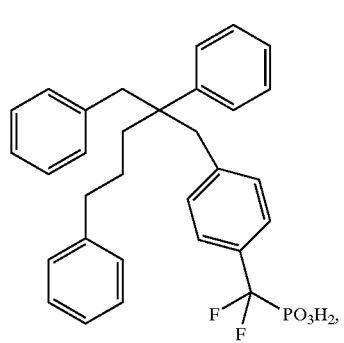
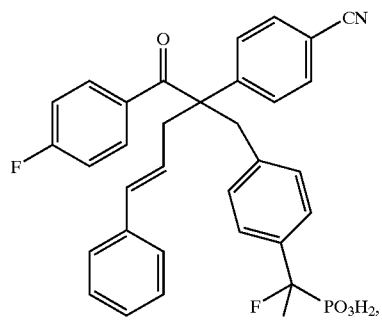
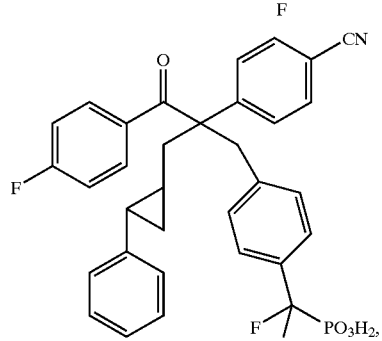
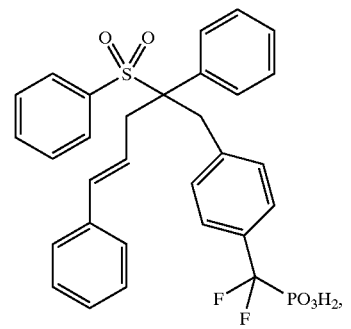
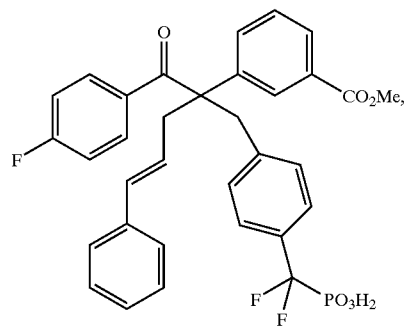
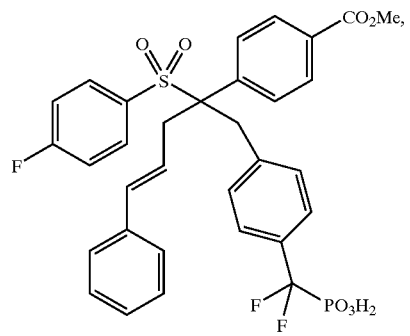

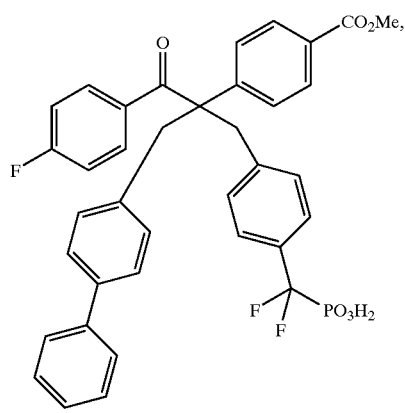
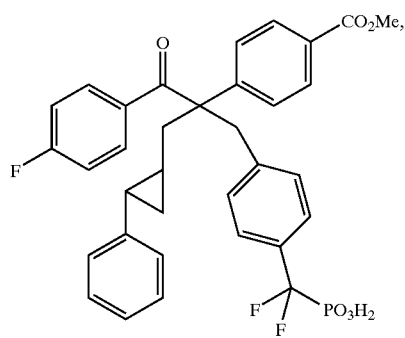
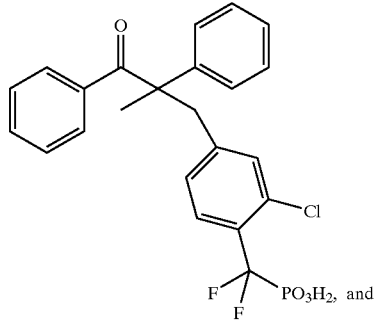
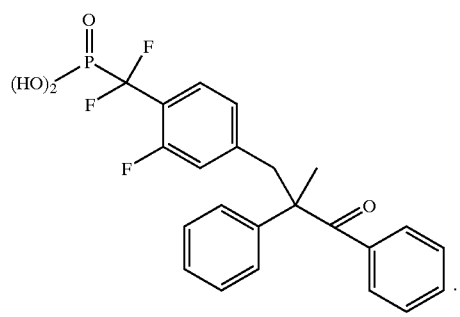
* * * * *

UNITED STATES PATENT AND TRADEMARK OFFICE
CERTIFICATE OF CORRECTION

PATENT NO. : 6,583,126 B2  
APPLICATION NO. : 09/745222  
DATED : June 24, 2003  
INVENTOR(S) : Leblanc et al.

Page 1 of 1

It is certified that error appears in the above-identified patent and that said Letters Patent is hereby corrected as shown below:

On the cover sheet:

(73) Assignee: delete "Merck Erosst Canada & Co., Kirkland" and replace with -- Merck Frosst Canada & Co., Kirkland --

Signed and Sealed this

Eighth Day of August, 2006

JON W. DUDAS  
*Director of the United States Patent and Trademark Office*